United States Patent
Mandell et al.

(10) Patent No.: US 11,542,544 B2
(45) Date of Patent: *Jan. 3, 2023

(54) POLYNUCLEOTIDE ENRICHMENT AND AMPLIFICATION USING CRISPR-CAS OR ARGONAUTE SYSTEMS

(71) Applicant: Illumina, Inc., San Diego, CA (US)

(72) Inventors: Jeffrey G. Mandell, San Diego, CA (US); Molly He, San Diego, CA (US)

(73) Assignee: Illumina, Inc., San Diego, CA (US)

(*) Notice: Subject to any disclaimer, the term of this patent is extended or adjusted under 35 U.S.C. 154(b) by 478 days.

This patent is subject to a terminal disclaimer.

(21) Appl. No.: 16/099,953

(22) PCT Filed: May 10, 2017

(86) PCT No.: PCT/US2017/032021
§ 371 (c)(1),
(2) Date: Mar. 28, 2019

(87) PCT Pub. No.: WO2017/197027
PCT Pub. Date: Nov. 16, 2017

(65) Prior Publication Data
US 2019/0136303 A1    May 9, 2019

Related U.S. Application Data

(60) Provisional application No. 62/335,012, filed on May 11, 2016.

(51) Int. Cl.
C12Q 1/68        (2018.01)
C12Q 1/6844    (2018.01)
C12Q 1/686      (2018.01)

(52) U.S. Cl.
CPC .......... *C12Q 1/6844* (2013.01); *C12Q 1/686* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,883,750 A | 11/1989 | Whiteley et al. |
| 5,034,506 A | 7/1991 | Summerton et al. |
| 5,432,272 A | 7/1995 | Benner |
| 5,476,930 A | 12/1995 | Letsinger et al. |
| 5,523,204 A | 6/1996 | Singer et al. |
| 5,536,649 A | 7/1996 | Fraiser et al. |
| 5,591,609 A | 1/1997 | Auerbach |
| 5,593,826 A | 1/1997 | Fung et al. |
| 5,614,389 A | 3/1997 | Auerbach |
| 5,624,825 A | 4/1997 | Walker et al. |
| 5,631,147 A | 5/1997 | Lohman et al. |
| 5,648,211 A | 7/1997 | Fraiser et al. |
| 5,733,752 A | 3/1998 | Lohman et al. |
| 5,744,311 A | 4/1998 | Fraiser et al. |
| 5,756,702 A | 5/1998 | Lohman et al. |
| 5,773,733 A | 6/1998 | Tuan et al. |
| 5,786,183 A | 7/1998 | Ryder et al. |
| 5,834,202 A | 11/1998 | Auerbach |
| 5,849,547 A | 12/1998 | Cleuziat et al. |
| 5,871,921 A | 2/1999 | Landegren et al. |
| 5,874,260 A | 2/1999 | Cleuziat et al. |
| 5,916,779 A | 6/1999 | Pearson et al. |
| 6,063,604 A | 5/2000 | Wick et al. |
| 6,087,133 A | 7/2000 | Dattagupta et al. |
| 6,124,120 A | 9/2000 | Lizardi |
| 6,210,891 B1 | 4/2001 | Nyren et al. |
| 6,214,587 B1 | 4/2001 | Dattagupta et al. |
| 6,218,151 B1 | 4/2001 | Cleuziat et al. |
| 6,238,868 B1 | 5/2001 | Carrino et al. |
| 6,251,639 B1 | 6/2001 | Kurn |
| 6,258,568 B1 | 7/2001 | Nyren |
| 6,274,320 B1 | 8/2001 | Rothberg et al. |
| 6,280,949 B1 | 8/2001 | Lizardi |
| 6,309,833 B1 | 10/2001 | Edman et al. |
| 6,326,173 B1 | 12/2001 | Edman et al. |
| 6,410,278 B1 | 6/2002 | Notomi et al. |
| 6,448,017 B1 | 9/2002 | Auerbach |
| 7,001,792 B2 | 2/2006 | Sauer et al. |
| 7,057,026 B2 | 6/2006 | Barnes et al. |
| 7,115,400 B1 | 10/2006 | Adessi et al. |

(Continued)

FOREIGN PATENT DOCUMENTS

| | | |
|---|---|---|
| AU | 00/29442 | 10/2000 |
| WO | WO 91/06678 | 5/1991 |

(Continued)

OTHER PUBLICATIONS

Gao et al. DNA-guided genome editing using the Natronobacterium gregoryi Argoanute. Nature Biotechnology, vol. 34, No. 7, pp. 768-773, 2016.*
Balachandran et al. Isothermal nucleic acid amplification technologies for point-of-care diagnostics: a critical review, Lab on a Chip, vol. 12, 2012. pp. 2469-2486.
Beloglazova et al. Structure and activity of the Cas3 HD nuclease MJ0384, an effector enzyme of the CRISPR interference, The Embo Journal vol. 30, No. 22, 2011, pp. 4616-4627.
Bentley et al. Accurate whole human genome sequencing using reversible terminator chemistry, Nature, vol. 456, 2008. pp. 53-59.
Bettegowda et al. Detection of Circulating Tumor DNA in Early-and Late-Stage Human Malignancies, Sci Transl Med, 2014, pp. 1-25.

(Continued)

*Primary Examiner* — Suryaprabha Chunduru
(74) *Attorney, Agent, or Firm* — Knobbe, Martens, Olson & Bear, LLP

(57) ABSTRACT

A method for enriching or amplifying a target nucleic acid including providing a system having a guide nucleic acid, and a Cas or Argonaute protein or a variant thereof. The guide nucleic acid contains a target-specific nucleotide region substantially complementary to a region of the target nucleic acid, and contacting the target nucleic acid with the system to form a complex.

20 Claims, 3 Drawing Sheets
Specification includes a Sequence Listing.

(56) References Cited

U.S. PATENT DOCUMENTS

| | | | |
|---|---|---|---|
| 7,211,414 | B2 | 5/2007 | Hardin et al. |
| 7,244,559 | B2 | 7/2007 | Rothberg et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 7,595,883 | B1 | 9/2009 | El Gamal et al. |
| 7,985,565 | B2 | 7/2011 | Mayer et al. |
| 2005/0191698 | A1 | 9/2005 | Chee et al. |
| 2008/0108082 | A1 | 5/2008 | Rank et al. |
| 2009/0026082 | A1 | 1/2009 | Rothberg et al. |
| 2009/0127589 | A1 | 5/2009 | Rothberg et al. |
| 2010/0120098 | A1 | 5/2010 | Grunenwald et al. |
| 2010/0137143 | A1 | 6/2010 | Rothberg et al. |
| 2010/0282617 | A1 | 11/2010 | Rothberg et al. |
| 2014/0323316 | A1* | 10/2014 | Drmanac ............ C12Q 1/6806 506/2 |
| 2015/0225773 | A1* | 8/2015 | Farmer ............ C12N 15/1003 506/26 |

FOREIGN PATENT DOCUMENTS

| | | | |
|---|---|---|---|
| WO | WO 95/23875 | 9/1995 | |
| WO | WO 00/28082 | 5/2000 | |
| WO | WO 00/56877 | 9/2000 | |
| WO | WO 02/16639 | 2/2002 | |
| WO | WO 04/018497 | 3/2004 | |
| WO | WO 07/123744 | 11/2007 | |
| WO | WO 2010/048605 | 4/2010 | |
| WO | WO2014/189628 | 11/2014 | |
| WO | WO-2014189628 A1 * | 11/2014 | ........... C12N 15/102 |
| WO | WO2015/140347 | 9/2015 | |
| WO | WO 2016/014409 | 1/2016 | |
| WO | WO 2016/077350 | 5/2016 | |

OTHER PUBLICATIONS

Brouns et al. Small CRISPR RNAs Guide Antiviral Defense in Prokaryotes, Science, vol. 321, 2008. pp. 960-964.

Chiu et al. Effects of Blood-Processing Protocols on Fetal and Total DNA Quantification in Maternal Plasma, Clinical Chemistry vol. 47, No. 9, 2001. pp. 1607-1613.

Cockroft et al. A Single-Molecule Nanopore Device Detects DNA Polymerase Activity With Single-Nucleotide Resolution, J. Am. Chem. Soc., vol. 130, No. 3, 2008. pp. 818-820.

Colegio et al. In Vitro Transposition System for Efficient Generation of Random Mutants of Campylobacter jejuni, Journal of Bacteriology, vol. 183, No. 7, 2001. pp. 2384-2388.

Craig. Transposon Tn7, Science, vol. 271, 1512, 1996, pp. 27-48.

Craig. V(D)J Recomination and Transposition: Closer than Expected, Review in: Curr Top Microbiol Immunol., vol. 204, 1996. pp. 27-48.

Deamer et al. Nanopores and nucleic acids: prospects for ultrarapid sequencing, Tibtech, vol. 18, 2000. pp. 147-151.

Deamer et al. Characterization of Nucleic Acids by Nanopore Analysis, Acc. Chem. Res. vol. 35, 2002. pp. 817-825.

Devine et al. Efficient integration of artificial transposons into plasmid targets in vitro: a useful tool for DNA mapping, sequencing and genetic analysis, Nucleic Acids Research, vol. 22, No. 18, 1994. pp. 3765-3772.

Dhallan et al. Methods to increase the percentage of free fetal DNA recovered from the maternal circulation, The Journal of the American Medical Association, vol. 291 (9), 2004. pp. 1114-1119.

Englisch, Chemically Modified Olionucleotides as Probes and Inhibitors. Chem. Int. Ed. Engl. 30:613-29, 1991.

Gao et al. DNA-guided genome editing using the Natronobacterium gregoryi Argonaute, Nature Biotechnology, vol. 34, No. 7, 2016. pp. 768-773.

Gill, et al., Nucleic acid isothermal amplification technologies—a review. Nucleosides, Nucleotides, and Nucleic Acids, vol. 27, 2008. pp. 224-243.

Gloor. Gene Targeting in *Drosophila*, Methods Mol. Biol., vol. 260, 2004. pp. 97-114.

Goryshin et al. Tn5 in Vitro Transposition, The Journal of Biological Chemistry, vol. 273, No. 13, 1998. pp. 7367-7374.

Haft et al. A Guild of 45 CRISPR-Associated (Cas) Protein Families and Multiple CRISPR/Cas Subtypes Exist in Prokaryotic Genomes, PLoS Computational Biology, vol. 1, Issue 6, e60, 2005.

Hale et al. RNA-Guided RNA Cleavage by a CRISPR RNA-Cas Protein Complex, Cell, vol. 139, 2009. pp. 945-956.

Healy. Nanopore-based single-molecule DNA analysis, Nanomed, vol. 2, 2007. pp. 459-481.

Hock et al. Protein Family Review: The Argonaute protein family, Genome Biology, vol. 9, No. 210, 2008. pp. 210.1-210.8.

Howard et al. Helicase dissociation and annealing of RNA-DNA hybrids by *Escherichia coli* Cas3 protein, Biochem. J., vol. 439, 2011. pp. 89-95.

Ichikawa et al. In Vitro Transposition of Transposon Tn3*, The Journal of Biological Chemistry, vol. 265, No. 31, 1990. pp. 18829-18832.

Jinek et al. A Programmable Dual-RNA-Guided DNA Endonuclease in Adaptive Bacterial Immunity, Science, vol. 337, No. 816, 2012. pp. 816-821.

Jore et al. Structural basis for CRISPR RNA-guided DNA recognition by Cascade, Nature Structural & Molecular Biology, vol. 18, No. 5, 2011. pp. 529-537.

Kirby et al. Cryptic plasmids of Mycobacterium avium: Tn552 to the rescue, Molecular Microbiology, vol. 43, No. 1, 2002. pp. 173-186.

Kleckner et al., Tn10 and IS10 Transposition and Chromosome Rearrangements: Mechanism and Regulation in Vivo and In Vitro Curr Top Microbiol Immunol., vol. 204, 1996. pp. 49-82.

Korlach et al. Selective aluminum passivation for targeted immobilization of single DNA polymerase molecules in zero-mode waveguide nanostructures, PNAS, vol. 105, No. 4, 2008. pp. 1176-1181.

Koshkin et al. LNA (Locked Nucleic Acids): Synthesis of the adenine, cytosine, guanine, 5-methlcytosine, thymine and uracil bicyclonucleoside monomers, oligomerisation, and unprecedented nucleic acid recognition, Tetrahedron, vol. 54:3607-30, 1998.

Lampe et al. A purified mariner transposase is sufficient to mediate transposition in vitro, The EMBO Journal, vol. 15, No. 19, 1996. pp. 5470-5479.

Legler et al. Workshop report on the extraction of foetal DNA from maternal plasma, Prenatal Diagnosis 27, vol. 9, 2007. pp. 824-829.

Levene et al. Zero-Mode Waveguides for Single-Molecule Analysis at High Concentrations, Science, vol. 299, 2003. pp. 682-686.

Li et al. DNA Molecules and Configurations in a Solid-State Nanopore Microscope, Nature Materials, 2:611-615 (2003).

Li et al. Size Separation of Circulatory DNA in Maternal Plasma Permits Ready Detection of Fetal DNA Polymorphisms, Clinical Chemistry, vol. 50, No. 6, 2004. pp. 1002-1011.

Li et al. Detection of Paternally Inherited Fetal Point Mutations for • -Thalassemia Using Size-Fractionated Cell-Free DNA in Maternal Plasma, American Medical Association (JAMA), vol. 293, No. 14, 2005. pp. 843-849.

Lundquist et al. Parallel confocal detection of single molecules in real time, Optics Letters, vol. 33, No. 9, 2008. pp. 1026-1028.

Makarova et al. Evolution and classification of the CRISPR-Cas systems, Nature Reviews: Microbiology, vol. 9, 2011. pp. 467-477.

Marraffini et al. CRISPR Interference Limits Horizontal Gene Transfer in *Staphylococci* by Targeting DNA, Science, vol. 322, 2008. pp. 1843-1845.

Mizuuchi. In Vitro Transposition of Bacteriophage Mu: Biochemical Approach to a Novel Replication Reaction, Cell, vol. 35, 785, 1983, pp. 785-794.

Mullis et al. Specific Enzymatic Amplification of DNA In Vitro: The Polymerase Chain Reaction, Cold Spring Harbor Symposia on Quantitative Biology, vol. LI, 1986. pp. 263-273.

Ohtsubo and Sekine. Bacterial Insertion Sequences, Curr.Top. Microbiol. Immunol., vol. 204, 1996. pp. 1-26.

Plasterk. The Tc1/mariner Transposon Family, Curr Top Microbiol Immunol., vol. 204, 1996. pp. 125-143.

(56) References Cited

OTHER PUBLICATIONS

Ronaghi et al. A Sequencing Method Based on Real-Time Pyrophosphate, Science, vol. 281, No. 5375, 1998. pp. 363-365.
Ronaghi et al. Pyrosequencing Sheds Light on DNA Sequencing, Genome Research, 2001. pp. 3-11.
Ronaghi et al. Real-Time DNA Sequencing Using Detection of Pyrophosphate Release, Analytical Biochemistry, 1996. pp. 84-89.
Savilahti et al. The phage Mu transpososome core: DNA requirements for assembly and function, The Embo Journal, vol. 14, No. 19, 1995. pp. 4893-4903.
Sinkunas et al. Cas3 is a single-stranded DNA nuclease and ATP-dependent helicase in the CRISPR/Cas immune system, The EMBO Journal, vol. 30, No. 7, 2011. pp. 1335-1342.
Soni et al. Progress toward Ultrafast DNA Sequencing Using Solid-State Nanopores, Clinical Chemistry, vol. 53, No. 11, 2007. pp. 1996-2001.
Tyagi et al. Molecular Beacons: Probes that Fluoresce upon Hybridization, Nature Biotechnology, vol. 14, 1996. pp. 303-306.
Verma et al. Modified Oligonucleotides: Synthesis and Strategy for Users, Annu. Rev. Biochem., vol. 67, 1998. pp. 99-134.
Wetmur et al. Kinetics of Renaturation of DNA, J. Mol. Biol., vol. 31, 1968. pp. 349-370.
Zhang et al. Nucl. Acids Res., 42, Issue 4, Feb. 1, 2014, pp. 2448-2459.

\* cited by examiner

Standard P5 & P7:
P5 seq: 5' AATGATACGGCGACCACCGAGATCTACAC 3' (SEQ ID No. 1)
P7 seq: 5' CAAGCAGAAGACGGCATACGAGAT 3' (SEQ ID No. 2)

PAM-Modified P5 & P7:
P5 seq: 5' CCN AATGATACGGCGACCACCGAGATCTACAC 3' (SEQ ID No. 3)
P7 seq: 5' CCN CAAGCAGAAGACGGCATACGAGAT 3' (SEQ ID No. 4)

Truncated, PAM-Modified P5 & P7:
P5 seq: 5' CCN AATGATACGGCGACCACC~~GAGATCTACAC~~ 3' (SEQ ID No. 5)
P7 seq: 5' CCN CAAGCAGAAGACGGCATA~~CGAGAT~~ 3' (SEQ ID No. 6)

Guide RNAs:
P5 targeting: 5' UCGGUGGUCGCCGUAUCAUU 3' (SEQ ID No. 7)
P7 targeting: 5' CGUAUGCCGUCUUCUGCUUG 3' (SEQ ID No. 8)

Figure 1A

POLYNUCLEOTIDE ENRICHMENT AND AMPLIFICATION USING CRISPR-CAS OR ARGONAUTE SYSTEMS

RELATED APPLICATIONS

This application is the U.S. National Phase of Int. App. No. PCT/US2017/032021 entitled "POLYNUCLEOTIDE ENRICHMENT AND AMPLIFICATION USING ARGONAUTE SYSTEMS" filed May 10, 2017 which published in English on Nov. 16, 2017 as WO 2017/197027 which claims priority to U.S. Prov. No. 62/33502 filed May 11, 2016 which are each incorporated by reference in its entirety.

REFERENCE TO SEQUENCE LISTING

The present application is being filed along with a Sequence Listing in electronic format. The Sequence Listing is provided as a file entitled ILLINC472NPSEQLIST, created Sep. 10, 2021, which is approximately 3.6 kb in size. The information in the electronic format of the Sequence Listing is incorporated herein by reference in its entirety.

The present disclosure relates generally to methods for enriching or amplifying polynucleotides, and more specifically to methods for enriching or amplifying polynucleotides using CRISPR-Cas or Argonaute systems and applications thereof.

BACKGROUND

There are a variety of methods and applications for which it is desirable to enrich or amplify a target polynucleotide among a population of polynucleotides, e.g., among whole genome.

Many of the methods currently used for sequence-specific DNA enrichment involve multiple steps and require relatively large amounts of sample nucleic acids, and usually are difficult, tedious, laborious, time-consuming, inefficient, and costly. In addition, methods currently used for targeted enrichment of double-stranded DNA require creating a single-stranded DNA prior to the sequence specific targeting. They also require longer time for hybridizing probes to target DNA. Thus, there exists a need for new methods that enable rapid and efficient sequence-specific polynucleotide enrichment.

Nucleic acid amplification is a key step of many nucleic acid based processes such as nucleic acid sequencing. Most currently used nucleic acid amplification methods, e.g., those used in cluster generation in the next generation sequencing, require both temperature cycling and fluid exchanges. Isothermal amplification, on the other hand, can be time and energy efficient by eliminating temperature ramp and equilibration times. Several isothermal amplification methods have been developed, e.g., recombinase polymerase amplification (RPA) based isothermal amplification. These isothermal amplification systems usually lack the desired speed and efficiency ideally suitable for some applications. Furthermore, some systems require additional enzymes and reagents including ATP. Thus, there remains a need in the art for convenient, rapid, and efficient isothermal nucleic acid amplification methods.

CRISPR-Cas and related proteins are discussed in PCT Publ. Nos. WO2016/014409 and WO2016/077350, which are hereby incorporated by reference in their entireties.

The present disclosure addresses these and other needs by providing methods for enriching or amplifying nucleic acid using CRISPR-Cas or Argonaute systems. Related advantages are provided as well.

SUMMARY

The present disclosure provides methods for enriching or amplifying polynucleotides, and more specifically to methods for enriching or amplifying a target DNA sequence using endonuclease systems, e.g., CRISPR-Cas systems or Argonaute systems, and applications thereof.

In one aspect, provided herein are methods for amplifying a target double-stranded nucleic acid using CRISPR-Cas systems.

In certain embodiments, provided herein is a method for amplifying a target double-stranded nucleic acid including: (a) providing a system having: a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; (b) contacting the target double-stranded nucleic acid with the system to form a complex; (c) hybridizing a primer to a second strand of the target double-stranded nucleic acid, the primer containing a sequence complementary to a region of the second strand of the target double-stranded nucleic acid, and (d) extending a nucleic acid complementary to the second strand of the target double-stranded nucleic acid from the primer using a polymerase.

In some embodiments, the method provided herein further including repeating step (c) to step (d) for one or more times, e.g., until a desired degree of amplification is reached. In some embodiments, the method provided herein further including repeating step (a) to step (d) until a desired degree of amplification is reached.

In some embodiments, the target nucleic acid provided herein is a double-stranded DNA (dsDNA). In some embodiments, the target nucleic acid is a double-stranded RNA (dsRNA).

In some embodiments, the system is a Type I CRISPR-Cas system or a derivative thereof. In some embodiments, the system is a Type II CRISPR-Cas system or a derivative thereof. In some embodiments, the system is a Type III CRISPR-Cas system or a derivative thereof.

In some embodiments, the system further comprises a trans-activating crRNA (tracrRNA) or a derivative thereof. In some embodiments, the crRNA or the derivative thereof is a polynucleotide comprising a crRNA polynucleotide fused to a tracrRNA polynucleotide.

In some embodiments, the first strand of the target double-stranded nucleic acid contains a sequence complementary to a 5'-NGG protospacer-adjacent motif (PAM).

In some embodiments, the first strand of the target double-stranded nucleic acid contains a universal sequence, and wherein the crRNA or the derivative thereof contains a sequence complementary to a region of the universal sequence. In some embodiments, the primer contains a sequence of a region of the universal sequence.

In some embodiments, the universal sequence has a sequence of SEQ ID No. 3. In some embodiments, the crRNA contains a sequence of SEQ ID No. 7. In some embodiments, the universal sequence has a sequence of SEQ ID No. 5.

In some embodiments, the universal sequence has a sequence of SEQ ID No. 4. In some embodiments, the crRNA contains a sequence of SEQ ID No. 8. In some embodiments, the universal sequence has a sequence of SEQ ID No. 6.

In some embodiments, the Cas protein or the variant thereof is a Cas9 protein or a variant thereof. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, the first mutation is D10A and the second mutation is H840A. In some embodiments, the Cas protein or the variant thereof is a Cascade protein or a variant thereof. In some embodiments, the Cas protein or the variant thereof is a Cas3 protein or a variant thereof.

In some embodiments, the polymerase is a strand-displacing polymerase. In some embodiments, the polymerase is selected from a group consisting of Bst, Bsu, and Phi29.

In some embodiments, the method provided herein further comprises: applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments, and incorporating a universal primer sequence into each of the plurality of target nucleic acid fragments, wherein the crRNA or the derivative thereof contains a target-specific nucleotide region complementary to a region of the universal primer.

In some embodiments, the universal primer is incorporated into the plurality of target nucleic acid fragments by a PCR reaction. In some embodiments, the universal primer has sequence complementary to a 5'-NGG protospacer-adjacent motif (PAM).

In some embodiments, the universal sequence has a sequence of SEQ ID No. 3. In some embodiments, the crRNA contains a sequence of SEQ ID No. 7. In some embodiments, the universal sequence has a sequence of SEQ ID No. 5.

In some embodiments, the universal primer has a sequence of SEQ ID No. 4. In some embodiments, the crRNA contains a sequence of SEQ ID No. 8. In some embodiments, the universal sequence has a sequence of SEQ ID No. 6.

In some embodiments, two universal primers are incorporated into two ends of each of the plurality of target nucleic acid fragments. In some embodiments, the two universal primers have sequences of SEQ ID No. 3 and SEQ ID No. 4. In some embodiments, the two universal primers have sequences of SEQ ID No. 5 and SEQ ID No. 6.

In some embodiments, the target double-stranded nucleic acid is linearly amplified. In some embodiments, the target double-stranded nucleic acid is exponentially amplified.

In some embodiments, provided herein is a method for amplifying a target double-stranded nucleic acid comprising: (a) providing a first system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a target-specific nucleotide region complementary to a region of a first strand of the target double-stranded nucleic acid; (b) providing second system having: a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, the method provided herein further includes repeating step (a) and step (e) for one or more times, e.g., until a desired degree of amplification is reached.

In some embodiments, the target nucleic acid is a double-stranded DNA (dsDNA). In some embodiments, the target nucleic acid is a double-stranded RNA (dsRNA).

In some embodiments, the first system or the second system is a Type I CRISPR-Cas system or a derivative thereof. In some embodiments, the first system or the second system is a Type II CRISPR-Cas system or a derivative thereof. In some embodiments, the first system or a second system is a Type III CRISPR-Cas system or a derivative thereof.

In some embodiments, the first system or the second system further comprises a trans-activating crRNA (tracrRNA) or a derivative thereof. In some embodiments, the crRNA or the derivative thereof of the first system or the second system is a polynucleotide comprising a crRNA polynucleotide fused to a tracrRNA polynucleotide. In some embodiments, the first strand and the second strand of the target double-stranded nucleic acid contain a sequence complementary to a 5'-NGG protospacer-adjacent motif (PAM).

In some embodiments, the first strand of the target double-stranded nucleic acid contains a first universal sequence, and wherein the crRNA or the derivative thereof of the first system contains a sequence complementary to a region of the first universal sequence, and the second strand of the target double-stranded nucleic acid contains a second universal sequence, and wherein the crRNA or the derivative thereof of the second system contains a sequence complementary to a region of the second universal sequence.

In some embodiments, the first primer contains a sequence of a region of the first universal sequence, and the second primer contains a sequence of a region of the second universal sequence. In some embodiments, the first universal sequence (which contains a first primer) has a sequence of SEQ ID No. 3, the crRNA or the derivative thereof of the first system contains a sequence of SEQ ID No. 7, and the first primer contains a sequence of SEQ ID No. 5, and the second universal sequence (which contains a second primer) has a sequence of SEQ ID No. 4, the crRNA or derivative thereof of the second system contains a sequence of SEQ ID No. 8, and the second primer contains a sequence of SEQ ID No. 6.

In some embodiments, the Cas protein or the variant thereof of the first system or the second system is a Cas9 protein or a variant thereof. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, the first mutation is D10A and the second mutation is H840A. In some embodiments, the Cas protein or the variant thereof of the first system or the second system is a Cascade protein or a variant thereof. In some embodiments, the Cas protein or the variant thereof of the first system or the second system is a Cas3 protein or a variant thereof.

In some embodiments, the polymerase is a strand-displacing polymerase. In some embodiments, the polymerase is selected from a group consisting of Bst, Bsu, and Phi29.

In some embodiments, the target nucleic acid is genomic DNA. In some embodiments, the target nucleic acid contains chromosomal DNA or a fragment thereof. In some embodiments, the target nucleic acid comprises a genome or a partial genome.

In some embodiments, the method provided herein further includes sequencing the target nucleic acid or target nucleic acid fragments. In some embodiments, the sequencing comprises use of one or more of sequencing by synthesis, bridge PCR, chain termination sequencing, sequencing by hybridization, nanopore sequencing, and sequencing by ligation.

In another aspect, provided herein are methods for amplifying a target double-stranded nucleic acid using Argonaute systems.

In certain embodiments, provided herein is a method for amplifying a target double-stranded nucleic acid including: (a) providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of a first strand of the target double-stranded nucleic acid; (b) contacting the target double-stranded nucleic acid with the system to form a complex; (c) hybridizing a primer to a second strand of the target double-stranded nucleic acid, the primer containing a sequence complementary to a region of the second strand of the target double-stranded nucleic acid, and (d) extending a nucleic acid complementary to the second strand of the target double-stranded nucleic acid from the primer using a polymerase.

In some embodiments, the method provided herein further including repeating step (c) to step (d) for one or more times, e.g., until a desired degree of amplification is reached. In some embodiments, the method provided herein further including repeating step (a) to step (d) until a desired degree of amplification is reached.

In some embodiments, the target nucleic acid provided herein is a double-stranded DNA (dsDNA). In some embodiments, the target nucleic acid is a double-stranded RNA (dsRNA).

In some embodiments, the 5' phosphorylated single-stranded nucleic acid is a single-stranded DNA (guide DNA or gDNA). In some embodiments, the 5' phosphorylated single-stranded nucleic acid is a single-stranded DNA of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the Argonaute protein is *Natronobacterium gregorgi* Argonaute (Ng Argonaute). In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the first strand of the target double-stranded nucleic acid contains a universal sequence, and wherein the gDNA or the derivative thereof contains a sequence complementary to a region of the universal sequence. In some embodiments, the primer contains a sequence of a region of the universal sequence.

In some embodiments, the polymerase is a strand-displacing polymerase. In some embodiments, the polymerase is selected from a group consisting of Bst, Bsu, and Phi29.

In some embodiments, the method provided herein further comprises: applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments.

In some embodiments, the target double-stranded nucleic acid is linearly amplified. In some embodiments, the target double-stranded nucleic acid is exponentially amplified.

In some embodiments, provided herein is a method for amplifying a target double-stranded nucleic acid comprising: (a) providing a first system having: a 5' phosphorylated single-stranded nucleic acid or a derivative thereof, and a first Argonaute protein or a variant thereof, wherein the first 5' phosphorylated single-stranded nucleic acid or the derivative thereof contains a target-specific nucleotide region complementary to a region of a first strand of the target double-stranded nucleic acid; (b) providing second system having: a second 5' phosphorylated single-stranded nucleic acid or a derivative thereof, and a second Argonaute protein or a variant thereof, wherein the second 5' phosphorylated single-stranded nucleic acid or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, the method provided herein further includes repeating step (a) and step (e) for one or more times, e.g., until a desired degree of amplification is reached.

In some embodiments, the target nucleic acid is a double-stranded DNA (dsDNA). In some embodiments, the target nucleic acid is a double-stranded RNA (dsRNA).

In some embodiments, the 5' phosphorylated single-stranded nucleic acid is a single-stranded DNA (guide DNA or gDNA). In some embodiments, the 5' phosphorylated single-stranded nucleic acid is a single-stranded DNA of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the Argonaute protein is *Natronobacterium gregorgi* Argonaute (Ng Argonaute). In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the first strand of the target double-stranded nucleic acid contains a first universal sequence, and wherein the gDNA or the derivative thereof of the first system contains a sequence complementary to a region of the first universal sequence, and the second strand of the target double-stranded nucleic acid contains a second universal sequence, and wherein the gDNA or the derivative thereof of the second system contains a sequence complementary to a region of the second universal sequence.

In some embodiments, the first primer contains a sequence of a region of the first universal sequence, and the second primer contains a sequence of a region of the second universal sequence.

In some embodiments, the polymerase is a strand-displacing polymerase. In some embodiments, the polymerase is selected from a group consisting of Bst, Bsu, and Phi29.

In some embodiments, the target nucleic acid is genomic DNA. In some embodiments, the target nucleic acid contains chromosomal DNA or a fragment thereof. In some embodiments, the target nucleic acid comprises a genome or a partial genome.

In some embodiments, the method provided herein further includes sequencing the target nucleic acid or target nucleic acid fragments. In some embodiments, the sequencing comprises use of one or more of sequencing by synthesis, bridge PCR, chain termination sequencing, sequencing by hybridization, nanopore sequencing, and sequencing by ligation.

In yet another aspect, provided herein are methods for enriching polynucleotides using CRISPR-Cas or Argonaute systems. In certain embodiments, provided herein is a method for enriching a target nucleic acid including providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method further includes separating the target nucleic acid from the complex. In some embodiments, the method further includes amplifying the targeted nucleic acid.

In some embodiments, the 5' phosphorylated single-stranded nucleic acid is a single-stranded DNA (guide DNA or gDNA). In some embodiments, the 5' phosphorylated single-stranded nucleic acid is a single-stranded DNA of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the target nucleic acid is a double-stranded DNA (dsDNA).

In some embodiments, the system is labeled. In some embodiments, the gDNA is labeled with biotin. In some embodiments, the method provided herein further includes adding streptavidin and thereby separating the complex. In some embodiments, the Argonaute protein or the derivative thereof is labeled with a capture tag.

In certain embodiments, provided herein is a method for enriching a target double-stranded nucleic acid including: providing an endonuclease system having: a 5' phosphorylated single-stranded nucleic acid or a derivative thereof, and an Argonaute protein or a variant thereof or a variant thereof, wherein the 5' phosphorylated single-stranded nucleic acid or the derivative thereof contains a target-specific nucleotide region complementary to a region of a first strand of the target double-stranded nucleic acid; contacting the target double-stranded nucleic acid with the endonuclease system to form a first complex; hybridizing a labeled nucleic acid to a second strand of the target double-stranded nucleic acid to form a second complex, the second strand of the target double-stranded nucleic acid being non-complementary to the 5' phosphorylated single-stranded nucleic acid or the derivative thereof, and separating the second complex and thereby enriching for the target nucleic acid.

In some embodiments, the method further includes separating the target nucleic acid from the complex. In some embodiments, the method further includes amplifying the targeted nucleic acid.

In some embodiments, the 5' phosphorylated single-stranded nucleic acids is a single-stranded DNA (guide DNA or gDNA). In some embodiments, the 5' phosphorylated single-stranded nucleic acids is a single-stranded DNA of less than 100 nucleotides. In some embodiments, the 5' phosphorylated single-stranded nucleic acids is a single-stranded DNA of less than 50 nucleotides. In some embodiments, the 5' phosphorylated single-stranded nucleic acids is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the target nucleic acid is a double-stranded DNA (dsDNA).

In some embodiments, the endonuclease system is labeled. In some embodiments, the 5' phosphorylated single-stranded nucleic acid is labeled with biotin. In some embodiments, the method provided herein further comprises adding streptavidin and thereby separating the complex.

In some embodiments, the Argonaute protein or the derivative thereof is labeled with a capture tag.

In certain embodiments, provided herein is a method for enriching a target nucleic acid including: obtaining a population of cell free DNA (cfDNA) from a subject's plasma or serum, the population of cell free DNA containing the target nucleic acid; providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the 5' phosphorylated single-stranded nucleic acids is a single-stranded DNA (guide DNA or gDNA). In some embodiments, the 5' phosphorylated single-stranded nucleic acids is a single-stranded DNA of less than 100 nucleotides. In some embodiments, the 5' phosphorylated single-stranded nucleic acids is a single-stranded DNA of less than 50 nucleotides. In some embodiments, the 5' phosphorylated single-stranded nucleic acids is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the target nucleic acid contains a single nucleotide variant (SNV). In some embodiments, the method further includes separating the target nucleic acid from the complex. In some embodiments, the method further includes amplifying the targeted nucleic acid. In some embodiments, the target nucleic acid is a double-stranded DNA (dsDNA).

In some embodiments, the system is labeled. In some embodiments, the gDNA is labeled with biotin. In some embodiments, the method provided herein further includes adding streptavidin and thereby separating the complex. In some embodiments, the Argonaute protein or the derivative thereof is labeled with a capture tag.

In some embodiments, the target nucleic acid is in a fetal cell faction of the cell free DNA, and wherein the cell free DNA is from maternal plasma. In some embodiments, the subject is a cancer patient.

In certain embodiments, provided herein is a method for detecting single nucleotide variant (SNV) including: obtaining a population of cell free DNA from a subject's plasma or serum; providing a first system having: a first 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a region of a first target nucleic acid, and wherein the first Argonaute protein has nuclease activity; cleaving the first target nucleic acid using the first endonuclease system, and amplifying a second target nucleic acid using Polymerase Chain Reaction (PCR), wherein the second target nucleic acid contains a single nucleotide variant version of the first target nucleic acid.

In some embodiments, the 5' phosphorylated single-stranded nucleic acid is a single-stranded DNA (guide DNA or gDNA). In some embodiments, the 5' phosphorylated single-stranded nucleic acid is a single-stranded DNA of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides.

In some embodiments, the method provided herein further includes: providing a second system having: a second 5' phosphorylated single-stranded nucleic acid or a derivative thereof, and a second Argonaute protein or a variant thereof, wherein the second 5' phosphorylated single-stranded nucleic acid or the derivative thereof contains a second target-specific nucleotide region complementary to a region of the second target nucleic acid; contacting the second target nucleic acid with the second endonuclease system to form a complex, and separating the complex and thereby enriching for the second target nucleic acid.

In some embodiments, the method provided herein further includes separating the second target nucleic acid from the complex. In some embodiments, the second target nucleic acid is a double-stranded DNA (dsDNA).

In some embodiments, the second system is labeled. In some embodiments, the second 5' phosphorylated single-stranded nucleic acid is labeled with biotin. In some embodiments, the method provided herein further includes adding streptavidin and thereby separating the complex. In some embodiments, the second Argonaute protein or the derivative thereof is labeled with a capture tag.

In some embodiments, the target nucleic acid is in a fetal cell faction of the cell free DNA, and wherein the cell free DNA is from maternal plasma. In some embodiments, the subject is a cancer patient.

In certain embodiments, provided herein is a method for labeling a target nucleic including providing a first system having: a 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a first region of the target nucleic acid, and wherein the first Argonaute protein is capable of generating a single-stranded nick; contacting a double-stranded nucleic acid containing the target nucleic acid with the first nuclease system to generate a first single-stranded nick at the first region of the target nucleic acid, and labeling the target nucleic acid.

In some embodiments, the method provided herein further includes separating the target nucleic acid through the labeling and thereby enriching the target nucleic acid. In some embodiments, the method provided herein further includes amplifying the target nucleic acid.

In some embodiments, the target nucleic acid is a double-stranded DNA (dsDNA).

In some embodiments, the method provided herein further includes performing a nick translation. In some embodiments, the nick translation is performed by using a nick translation polymerase selected from a group consisting of DNA Pol 1, Bst, and Taq. In some embodiments, the nick translation is performed in a reaction mixture containing biotinylated dNTPs. In some embodiments, the biotinylated dNTPs are biotinylated dUTPs. In some embodiments, the method provided herein further includes adding magnetic streptavidin beads to enrich biotinylated target nucleic acid.

In some embodiments, the method provided herein further includes providing a second system having: a second 5' phosphorylated single-stranded nucleic acid or a derivative thereof, and a second Argonaute protein or a variant thereof, wherein the second 5' phosphorylated single-stranded nucleic acid or the derivative thereof contains a second target-specific nucleotide region complementary to a second region of the target nucleic acid, and wherein the second Argonaute protein is capable of generating a single-stranded nick, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid.

In some embodiments, the first single-stranded nick and the second single-stranded nick are on the same strand of the target nucleic acid. In some embodiments, the space between the first single-stranded nick and the second single-stranded nick on the same strand of the target nucleic acid is 1 bp to 20 bp. In some embodiments, the method further includes performing a nick translation. In some embodiments, the nick translation is performed by using a nick translation polymerase Phi29.

In some embodiments, the first region of the target nucleic acid and the second region of the target nucleic acid are on different strands of the target nucleic acid. In some embodiments, the space between the first single-stranded nick and the second single-stranded nick is from 20 bp to 500 bp.

In some embodiments, the method provided herein further includes adding a capture probe; and exchanging a single-stranded nucleic acid product between the first single-stranded nick and the second single-stranded nick with the capture probe, wherein the capture probe is able to hybridize to a nucleic acid complementary to the single-stranded nucleic acid product.

In some embodiments, the sequence of the capture probe is 10% to 100% identical to the sequence of the single-stranded nucleic acid product. In some embodiments, the capture probe is a biotinylated probe. In some embodiments, the method provided herein further includes adding magnetic streptavidin beads to enrich the target nucleic acid. In some embodiments, the capture probe contains an overhang nucleotide sequence, the overhang nucleotide sequence is complementary to an oligonucleotide immobilized on a surface.

In some embodiments, the first single-stranded nick and the second single-stranded nick are on opposite strands of the target nucleic acid, thereby generating a first double-stranded nucleic acid break end.

In some embodiments, the method provided herein further includes ligating an adapter to the first double-stranded DNA break end. In some embodiments, the adapter is biotinylated. In some embodiments, the method provided herein further includes adding magnetic streptavidin beads to enrich the target nucleic acid.

In some embodiments, the method provided herein further includes providing a third system having: a third 5' phosphorylated single-stranded nucleic acid or a derivative thereof, and a third Argonaute protein or a variant thereof, wherein the third 5' phosphorylated single-stranded nucleic acid or the derivative thereof contains a third target-specific nucleotide region substantially complementary to a third region of the target nucleic acid, and wherein the third Argonaute protein is capable of generating a single-stranded nick; providing a fourth system having: a fourth 5' phosphorylated single-stranded nucleic acid or a derivative thereof, and a fourth Argonaute protein or a variant thereof, wherein the fourth 5' phosphorylated single-stranded nucleic acid or the derivative thereof contains a fourth target-specific nucleotide region substantially complementary to a fourth region of the target nucleic acid, and wherein the fourth Argonaute protein is capable of generating a single-stranded nick; and contacting the double-stranded nucleic acid containing the target nucleic acid with the third and fourth systems to generate a third single-stranded nick at the third region of the target nucleic acid and a fourth single-stranded nick at the fourth region of the target nucleic acid, wherein in the third single-stranded nick and the fourth single-stranded nick are on opposite strands of the target nucleic acid, thereby generating a second double-stranded nucleic acid break end, the second double-stranded nucleic acid break end being different from the first double-stranded nucleic acid break end. In some embodiments, the method further includes ligating an adapter to the second double-stranded nucleic acid break end.

In certain embodiments, provided herein is a method for enriching a target nucleic acid including: providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions of the target nucleic acid; contacting the target nucleic acid with the population of Argonaute proteins programmed with the set of 5' phosphorylated single-stranded nucleic acids to generate a series of nucleic acid fragments, and ligating adaptors to at least one of nucleic acid fragments, wherein the Argonaute proteins are capable of generating double-stranded DNA breaks.

In some embodiments, the set of 5' phosphorylated single-stranded nucleic acids contains 5' phosphorylated single-stranded nucleic acids complementary to two different regions of the target nucleic acid. In some embodiments, the target nucleic acid is a double-stranded DNA. In some embodiments, the target nucleic acid is a genomic DNA, a chromosomal DNA, a genome, or a partial genome.

In another aspect, provided herein is a method for sequencing a target nucleic acid including: providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions across the target nucleic acid; contacting the target nucleic acid with the population of Argonaute proteins programmed with the set of 5' phosphorylated single-stranded nucleic acids to generate a series of nucleic acid fragments, and sequencing the series of nucleic acid fragments.

In some embodiments, provided herein is a method for sequencing a target nucleic acids including: providing a plurality of populations of Argonaute proteins, each population of Argonaute proteins being programmed with a different set of 5' phosphorylated single-stranded nucleic acids, wherein each set of 5' phosphorylated single-stranded nucleic acids contains 5' phosphorylated single-stranded nucleic acids complementary to a different series of regions across the target nucleic acid, contacting the target nucleic acid with each of the plurality of populations of Argonaute proteins in a separate reaction to generate a different series of nucleic acid fragments, and sequencing the nucleic acid fragments.

In some embodiments, the plurality of populations of Argonaute proteins comprises three populations of Argonaute proteins, and wherein the nucleic acid fragments generated by each of the three populations of Argonaute proteins contain overlapping sequences with the nucleic acid fragments generated by at least another of the three populations of Argonaute proteins. In some embodiments, the Argonaute proteins are capable of generating double-stranded DNA breaks. In some embodiments, the target nucleic acid is a double-stranded DNA. In some embodiments, the target nucleic acid is a genomic DNA, a chromosomal DNA, a genome, or a partial genome. In some embodiments, the method further includes ligating an adapter to the nucleic acid fragments. In some embodiments, the method provided herein further includes diluting a DNA sample containing the target DNA to haploid content. In some embodiments, the sequencing the nucleic acid fragments comprises use of one or more of sequencing by synthesis, bridge PCR, chain termination sequencing, sequencing by hybridization, nanopore sequencing, and sequencing by ligation.

BRIEF DESCRIPTION OF THE DRAWINGS

FIG. 1A shows the primers designed according to the present methods for amplifying DNA fragments containing the entirety or portions of Illumina universal sequencing primer adaptors P5 and P7. The primers can be added using the Nextera (Illumina, Inc.) library preparation method.

DETAILED DESCRIPTION

Figure 1B:
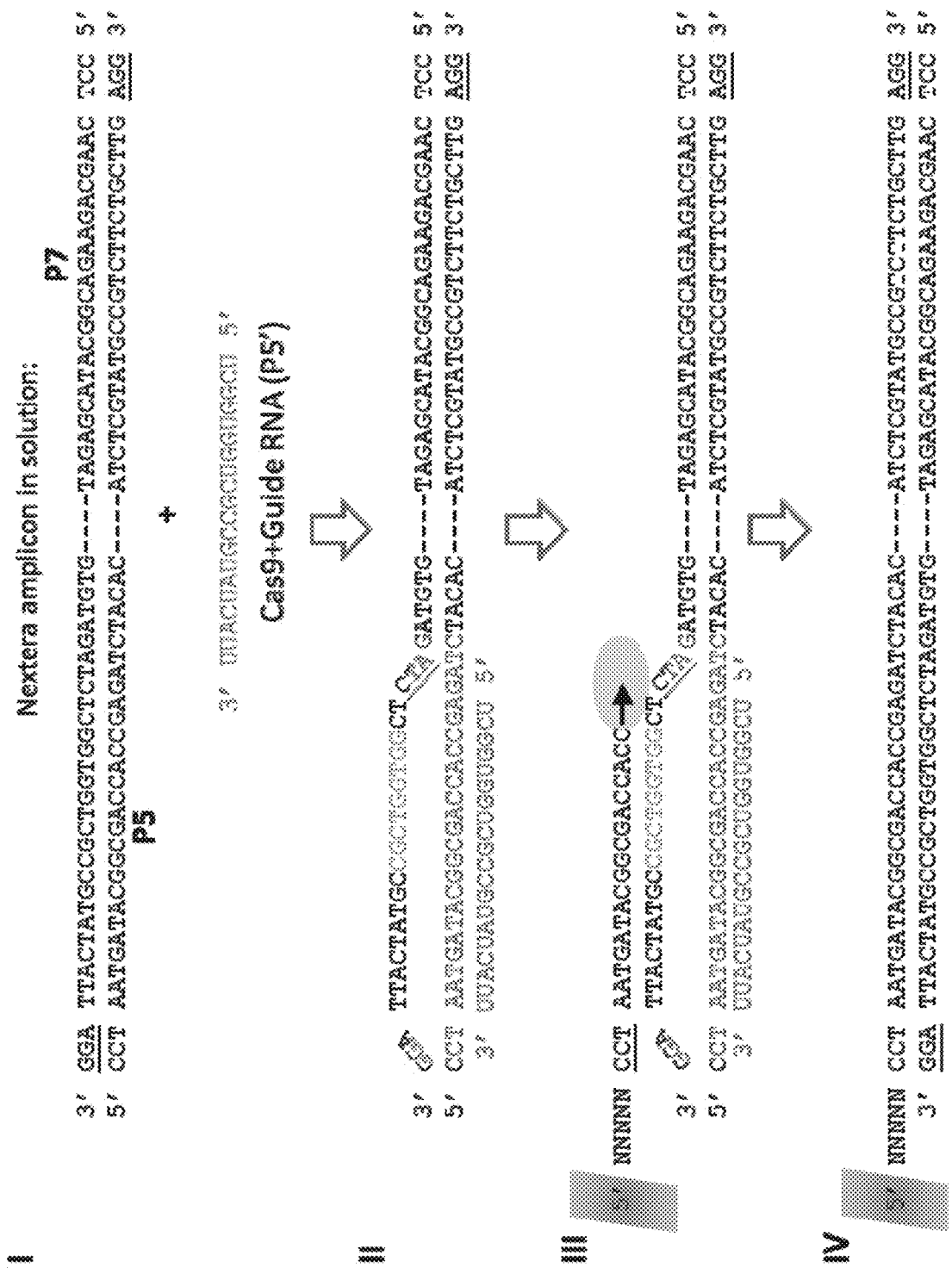
FIG. 1B illustrates one round of Cas9-mediated linear amplification using a crRNA targeting a modified P5 primer. 1B(I) depicts the DNA to be amplified which possesses appropriate primer sequences P5 and P7 (SEQ ID NO:09, CCTAATGATACGGCGACCACCGAGATCTACAC; and SEQ ID NO:10, ATCTCGTATGCCGTCTTCTGCTTGAGG). The guide RNA targeting P5, bound to Cas9, is also shown as P5' (SEQ ID NO:11, UUACUAUGCCGUGGUGGCU). 1B(II) shows the R loop created by Cas9 after the guide RNA (SEQ ID NO:11) has hybridized to the first strand. 1B(III) illustrates the immobilized P5 primer (SEQ ID NO: 12, CCTAATGATACGGCGACCACC) hybridizing to the displaced second strand, followed by polymerase extension. 1B(IV) shows the resulting extended primer P5 (SEQ ID NO:13 CCTAATGATACGGCGACCACCGAGATCTACAC, and SEQ ID NO:10). The resulting amplicon can be re-targeted by Cas9+crRNA as shown in step 1B(II).

The present disclosure provides methods for rapid and efficient enrichment or amplification of target nucleic acid using CRISPR-Cas or Argonaute systems.

Current target-specific enrichment protocols require that single-stranded nucleic acid be made prior to the target specific hybridization with probes. Among various advantages provided by the present disclosure, the present disclosure provides enrichment methods that can skip this step of generating single-stranded nucleic acid in the first place, and enable direct targeting to double-stranded nucleic acid, e.g., double-stranded DNA (dsDNA). Methods targeting directly to double-stranded DNA (either partly or completely double-stranded) have unique advantages over single-stranded enrichment strategies. For example, non-specific hybridization of single-stranded genomic DNA to targeted regions reduces specificity and often requires extensive stringency washing or other time-consuming steps; and single-stranded enrichment schemes often utilizes Cot-1 or other blocking DNA to reduce non-specific hybridization. These additives are not required from double-stranded DNA enrichment schemes, reducing both cost and number of required reagents. In addition, it is easier to make sequencing libraries from double-stranded DNA than from single-stranded DNA. As such, enrichment of double-stranded DNA allows library preparation (e.g., tagmentation) to occur after enrichment. For another example, since specificity (tree-like structures and non-specific hybridization is less of an issue with double-stranded DNA enrichment, potentially larger DNA fragments can be better specifically enriched compared to single-stranded DNA enrichment schemes. This is a particularly important advantage if one considers targeted sequencing in the context of haplotyping and assembly. Also, since longer DNA fragments can potentially be enriched, we have greater flexibility to where the target probe is designed. For example, we can avoid high polymorphic regions but still capture these regions. Also, fewer probes need to be used to capture large regions, reducing both capture probe cost and design.

In addition, the current protocols of target specific hybridization have slow kinetics and usually require high temperature. The present disclosure provides enzyme-driven sequence targeting methods that offer faster kinetics and easier workflow for enrichment. Because the hybridization to the target nucleic acid is enzyme driven in the present methods, the process can take place isothermally. In some embodiments, the method herein provides isothermal targeting of DNA at 20-37° C. Furthermore, the guide RNA, e.g., crRNA, in the system herein provides for sequence specificity as well as flexible programming that enables multiplex targeted enrichment (e.g., targeting multiple targeted regions with more probes made in various ways including IVT from oligo pool).

Nucleic acid amplification is a step of many nucleic acid based processes such as next generation sequencing. Currently the polymerase chain reaction (PCR) is the most widely used method for DNA amplification for, e.g., detection and identification of infectious diseases, genetic disorders and other research purposes. A PCR reaction typically uses two oligonucleotide primers, which are hybridized to the 3' ends of a duplex target nucleic acid sequence, and a DNA polymerase, which can extend the annealed primers by adding on deoxyribonucleoside triphosphates (dNTPs) to generate double-stranded nucleic acid products. Gill and Ghaemi, *Nucleosides, Nucleotides, and Nucleic Acids*, 2008, 27: 224-243. However, a PCR reaction requires thermocycling to separate the two DNA strands. Similarly, many currently used nucleic acid amplification methods, e.g., those used in cluster generation in the next generation sequencing, require both temperature cycling and fluid exchanges.

Several isothermal amplification methods have been developed in order to eliminate temperature ramp and equilibration times, such as recombinase polymerase amplification (RPA) based isothermal amplification, transcription mediated amplification, nucleic acid sequence-based amplification, signal mediated amplification of RNA, strand displacement amplification, rolling circle amplification, loop-mediated isothermal amplification of DNA, isothermal multiple displacement amplification, helicase-dependent amplification, single primer isothermal amplification, and circular helicase-dependent amplification, as described in Gill and Ghaemi, *Nucleosides, Nucleotides, and Nucleic Acids,* 2008, 27: 224-243.

For example, in a transcription mediated amplification (TMA), an RNA polymerase is used to make RNA from a promoter engineered in the primer region, and then a reverse transcriptase synthesizes cDNA from the primer. A third enzyme, e.g., Rnase H can then be used to degrade the RNA target from cDNA without the heat-denatured step. This amplification technique is very similar to Self-Sustained Sequence Replication (3SR) and Nucleic Acid Sequence Based Amplification (NASBA), but varies in the enzymes employed. Id. For another example, helicase-dependent amplification (HDA) utilizes a thermostable helicase (Tte-UvrD) rather than heat to unwind dsDNA to create single-strands that are then available for hybridization and extension of primers by polymerase. Reaction times have been shown to be over 1 hour to amplify products 70-120 base pairs in length. Id. For yet another example, a loop mediated amplification (LAMP) employs a thermostable polymerase with strand displacement capabilities and a set of four or more specific designed primers. Each primer is designed to have hairpin ends that, once displaced, snap into a hairpin to facilitate self-priming and further polymerase extension. In a LAMP reaction, though the reaction proceeds under isothermal conditions, an initial heat denaturation step is required for double-stranded targets. In addition, amplification yields a ladder pattern of various length products. Id. For yet another example, a strand displacement amplification (SDA) combines the ability of a restriction endonuclease to nick the unmodified strand of its target DNA and an exonuclease-deficient DNA polymerase to extend the 3' end at the nick and displace the downstream DNA strand. Id. Other exemplary isothermal amplification methods include, but not limited to, those described in Craw and Balachandran, *Lab Chip,* 2012, 12: 2469-2486.

However, these currently developed isothermal amplification systems usually lack the desired speed and efficiency ideally suitable for some applications. Furthermore, some systems require additional enzymes and reagents including ATP. Thus, there remains a need in the art for convenient, rapid, and efficient isothermal nucleic acid amplification methods.

The present disclosure addresses this and other needs by providing methods for enriching or amplifying nucleic acid using CRISPR-Cas or Argonautes systems. For example, one advantage provided by the present methods is that the system used herein, e.g., Cas protein, recognizes target nucleic acid without consuming ATP or energy investment, and thus the methods herein provide for cost and time efficient isothermal amplification methods.

The present disclosure also provides methods for enriching and/or detecting polynucleotide variants with higher sensitivity and specificity. Furthermore, the present invention also provides methods for targeted sequencing using CRISPR-Cas or Argonaute systems.

Definitions

As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the singular forms "a", "an" and "the" include plural referents unless the content clearly dictates otherwise. Thus, for example, reference to "a protein" includes a mixture of two or more proteins, and the like.

As used herein, the term "about" or "approximately" means within 5% of a given value or range.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid can be a polynucleotide or an oligonucleotide. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotides analogs. Nucleic acid typically ranges in size from a few monomeric units, e.g., 5-40, to several thousands of monomeric nucleotide units. Nucleic acids include, but are not limited to, genomic DNA, cDNA, hnRNA, mRNA, rRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "target nucleic acid" is intended to mean a nucleic acid that is the object of an analysis or action. The analysis or action includes subjecting the nucleic acid to copying, amplification, sequencing and/or other procedure for nucleic acid interrogation. A target nucleic acid can include nucleotide sequences additional to the target sequence to be analyzed. For example, a target nucleic acid can include one or more adapters, including an adapter that functions as a primer binding site, that flank(s) a target nucleic acid sequence that is to be analyzed. A target nucleic acid hybridized to a capture oligonucleotide or capture primer can contain nucleotides that extend beyond the 5' or 3' end of the capture oligonucleotide in such a way that not all of the target nucleic acid is amenable to extension.

As used herein, the term "target specific" when used in reference to a guide RNA or DNA, a crRNA or a derivative thereof, a 5' phosphorylated single-stranded nucleic acid, or other nucleotide is intended to mean a polynucleotide that includes a nucleotide sequence specific to a target polynucleotide sequence, namely a sequence of nucleotides capable of selectively annealing to an identifying region of a target polynucleotide, e.g., a target DNA. Target specific nucleotide can have a single species of oligonucleotide, or it can include two or more species with different sequences. Thus, the target specific nucleotide can be two or more sequences, including 3, 4, 5, 6, 7, 8, 9 or 10 or more different sequences. In one embodiment, a crRNA or the derivative thereof contains a target-specific nucleotide region complementary to a region of the target DNA sequence. In one embodiment, a crRNA or the derivative thereof may contain other nucleotide sequences besides a target-specific nucleotide region. In one embodiment, the other nucleotide sequences may be from a tracrRNA sequence. In one embodiment, a 5' phosphorylated single-stranded nucleic acid or the derivative thereof contains a target-specific nucleotide region complementary to a region of the target DNA sequence. In one embodiment, a 5' phosphorylated single-stranded nucleic acid or the derivative thereof may contain other nucleotide sequences besides a target-specific nucleotide region.

As used herein, the term "complementary" when used in reference to a polynucleotide is intended to mean a polynucleotide that includes a nucleotide sequence capable of selectively annealing to an identifying region of a target polynucleotide under certain conditions. As used herein, the term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions can also contribute to duplex stability. Conditions under which a polynucleotide anneals to complementary or substantially complementary regions of target nucleic acids are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968). Annealing conditions will depend upon the particular application, and can be routinely determined by persons skilled in the art, without undue experimentation.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions will typically include salt concentrations of less than about 1 M, more usually less than about 500 mM and may be less than about 200 mM. A hybridization buffer includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances, and may be determined routinely by those skilled in the art.

In the context of "polynucleotides," the terms "variant" and "derivative" as used herein refer to a polynucleotide that comprises a nucleotide sequence of a polynucleotide or a fragment of a polynucleotide, which has been altered by the introduction of nucleotide substitutions, deletions or additions. A variant or a derivative of a polynucleotide can be a fusion polynucleotide which contains part of the nucleotide sequence of a polynucleotide. The term "variant" or "derivative" as used herein also refers to a polynucleotide or a fragment thereof, which has been chemically modified, e.g., by the covalent attachment of any type of molecule to the polynucleotide. For example, but not by way of limitation, a polynucleotide or a fragment thereof can be chemically modified, e.g., by acetylation, phosphorylation, methylation, etc. The variants or derivatives are modified in a manner that is different from naturally occurring or starting nucleotide or polynucleotide, either in the type or location of the molecules attached. Variants or derivatives further include deletion of one or more chemical groups which are naturally present on the nucleotide or polynucleotide. A variant or a derivative of a polynucleotide or a fragment of a polynucleotide can be chemically modified by chemical modifications using techniques known to those of skill in the art, including, but not limited to specific chemical cleavage, acetylation, formulation, etc. Further, a variant or a derivative of a polynucleotide or a fragment of a polynucleotide can contain one or more dNTPs or nucleotide analogs. A polynucleotide variant or derivative may possess a similar or identical function as a polynucleotide or a fragment of a polynucleotide described herein. A polynucleotide variant or derivative may possess an additional or different function compared with a polynucleotide or a fragment of a polynucleotide described herein.

As used herein, the term "dNTP" refers to deoxynucleoside triphosphates. NTP refers to ribonucleotide triphosphates such as those used to synthesize crRNA or tracrRNA. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

As used herein, the term "nucleotide analogs" refers to synthetic analogs having modified nucleotide base portions, modified pentose portions, and/or modified phosphate portions, and, in the case of polynucleotides, modified internucleotide linkages, as generally described elsewhere (e.g., Scheit, *Nucleotide Analogs*, John Wiley, New York, 1980; Englisch, *Angew. Chem. Int. Ed. Engl.* 30:613-29, 1991; Agarwal, *Protocols for Polynucleotides and Analogs*, Humana Press, 1994; and S. Verma and F. Eckstein, *Ann. Rev. Biochem.* 67:99-134, 1998). Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., The Glen Report, 16(2):5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., *Organic Chem.*, 52:4202, 1987), and uncharged morpholino-based polymers having achiral intersubunit linkages (see, e.g., U.S.

Pat. No. 5,034,506). Some internucleotide linkage analogs include morpholidate, acetal, and polyamide-linked heterocycles.

The terms "polymerase chain reaction," or "PCR," as used herein, refers to a procedure wherein small amounts of a nucleic acid, e.g., RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, NY, 1989).

As used herein, the terms "ligation," "ligating," and grammatical equivalents thereof are intended to mean to form a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921, incorporated herein by reference in their entireties. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "adapter" is a single-stranded or a double-stranded nucleic acid molecule that can be linked to the end of other nucleic acids. In one embodiment, an adapter is a short, chemically synthesized, double-stranded nucleic acid molecule which can be used to link the ends of two other nucleic acid molecules. In one embodiment, an adaptor is a double-stranded nucleic acid (e.g., oligonucleotides) that comprises single-stranded nucleotide overhangs at the 5' and/or 3' ends. In some embodiments, the single-stranded overhangs are 1, 2 or more nucleotides. In some embodiments, adaptors comprise additional nucleic acid sequence for cloning or analysis of "inserts." In some embodiments, adaptors comprise labels or affinity tags for analysis or purification of "inserts." The term "insert" refers to a nucleic acid sequence of interest. In some embodiments, inserts are double-stranded DNAs that comprise single stranded nucleotide overhangs at the 5' and/or 3' ends. In some embodiments, the single stranded overhangs are 1, 2 or more nucleotides.

As used herein, the term "CRISPR-Cas system" refers to an enzyme system including a guide RNA sequence that contains a nucleotide sequence complementary or substantially complementary to a region of a target polynucleotide, and a protein with nuclease activity. CRISPR-Cas systems include Type I CRISPR-Cas system, Type II CRISPR-Cas system, Type III CRISPR-Cas system, and derivatives thereof. CRISPR-Cas systems include engineered and/or programmed nuclease systems derived from naturally accruing CRISPR-Cas systems. CRISPR-Cas systems may contain engineered and/or mutated Cas proteins. CRISPR-Cas systems may contain engineered and/or programmed guide RNA.

As used herein, the term "Argonaute system" refers to an enzyme system including a guide nucleic acid, e.g., a guide DNA, that contains a nucleotide sequence complementary or substantially complementary to a region of a target polynucleotide, and an Argonaute family protein or a variant thereof. Argonaute systems include engineered and/or programmed nuclease systems derived from naturally accruing Argonaute systems. Argonaute systems may contain engineered and/or mutated Argonaute proteins. Argonaute systems may contain engineered and/or programmed guide DNA.

As used herein, the term "guide RNA" refers to a RNA containing a sequence that is complementary or substantially complementary to a region of a target DNA sequence. A guide RNA may contain nucleotide sequences other than the region complementary or substantially complementary to a region of a target DNA sequence. A guide RNA may be a crRNA or a derivative thereof, e.g., a crRNA: tracrRNA chimera.

As used herein, the term "guide DNA" refers to a DNA containing a sequence that is complementary or substantially complementary to a region of a target DNA sequence. A guide DNA may contain nucleotide sequences other than the region complementary or substantially complementary to a region of a target DNA sequence.

As used herein, the term "nuclease" refers to an enzyme capable of cleaving the phosphodiester bonds between the nucleotide subunits of nucleic acids; the term "endonuclease" refers to an enzyme capable of cleaving the phosphodiester bond within a polynucleotide chain; and the term "nickase" refers to an endonuclease which cleaves only a single strand of a DNA duplex. The term "Cas9 nickase" refers to a nickase derived from a Cas9 protein, typically by inactivating one nuclease domain of Cas9 protein.

In the context of a polypeptide, the terms "variant" and "derivative" as used herein refer to a polypeptide that comprises an amino acid sequence of a polypeptide or a fragment of a polypeptide, which has been altered by the introduction of amino acid residue substitutions, deletions or additions. A variant or a derivative of a polypeptide can be a fusion protein which contains part of the amino acid sequence of a polypeptide. The term "variant" or "derivative" as used herein also refers to a polypeptide or a fragment of a polypeptide, which has been chemically modified, e.g., by the covalent attachment of any type of molecule to the polypeptide. For example, but not by way of limitation, a polypeptide or a fragment of a polypeptide can be chemically modified, e.g., by glycosylation, acetylation, pegylation, phosphorylation, amidation, derivatization by known protecting/blocking groups, proteolytic cleavage, linkage to a cellular ligand or other protein, etc. The variants or derivatives are modified in a manner that is different from naturally occurring or starting peptide or polypeptides, either in the type or location of the molecules attached. Variants or derivatives further include deletion of one or more chemical groups which are naturally present on the peptide or polypeptide. A variant or a derivative of a polypeptide or a fragment of a polypeptide can be chemically modified by chemical modifications using techniques known to those of skill in the art, including, but not limited to specific chemical cleavage, acetylation, formulation, metabolic synthesis of tunicamycin, etc. Further, a variant or a derivative of a polypeptide or a fragment of a polypeptide can contain one or more non-classical amino acids. A polypeptide variant or derivative may possess a similar or identical function as a polypeptide or a fragment of a polypeptide described herein. A polypeptide variant or derivative may possess an additional or different function compared with a polypeptide or a fragment of a polypeptide described herein.

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the charge-to-mass ratio, the mass, the amount, the absorbance, the fluorescence, or other property of the nucleic acid molecule or fragment thereof.

As used herein, the term "primer" refers to an oligonucleotide primer, whether natural or synthetic, which is capable of acting as a point of initiation of nucleic acid synthesis when placed under conditions in which primer extension (not limited in number of extended bases) is initiated. A primer can be a single-stranded oligodeoxyribonucleotide. The length of a primer can range from about 10 to about 50 nucleotides, for example 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides. A primer need not reflect the exact sequence of the template but must be sufficiently complementary to hybridize with a template for primer elongation to occur. A primer can be labeled, if desired, by incorporating a label that is detectable by, for example, spectroscopic, photochemical, biochemical, immunochemical, or chemical means. Exemplary labels include, but are not limited to biotin, amine, radiolabels (e.g., 32P), fluorescent dyes, electron-dense reagents, enzymes (as commonly used in ELISAS), or biotin.

As used herein, the term "linear amplification" refers to an amplification process that uses multiple cycles of primer extension reactions to amplify a target nucleic acid. With linear amplification, the abundance of a transcript increases proportionately with the number of cycles and scales linearly. An example of a linear amplification procedure is LCR, the aRNA method of Phillips and Eberwine, supra, and the linear amplification method described herein. Unlike exponential amplification, the amount of the amplification products does not grow exponentially. For example, in an ideal 4 hour linear amplification reaction whose copying rate is 2000 copies per minute, 2000 copies of template DNA will yield 960,000,000 copies.

As used herein, the term "exponential amplification" refers to an amplification procedure where the product (i.e., amplicon) doubles with every reaction cycle. "Exponential amplification" is a non-linear amplification that results in exponential growth in the number of nucleic acid copies present. For example, exponential amplification can occur when primer extension initiates from both ends of an amplicon in one amplification cycle. For example, PCR is an exponential amplification procedure. For example, in an ideal PCR reaction with 30 cycles, 2 copies of template DNA will yield $2^{30}$ or 1,073,741,824 copies.

As used herein, in the context of enriching a target polynucleotide, the term "enrich," "enriching", or "enrichment" refers to a process which results in a higher percentage of the target polynucleotide in a polynucleotide population. In one embodiment, the percentage increases about 5%, 10%, 20%, 30%, 40%, 50%, 60%, 70%, 80%, 90% or 100%. In one embodiment, the percentage increases about 2 fold, 5 fold, 10 fold, 50 fold, or 100 fold. In one embodiment, the target polynucleotide is substantially isolated from the polynucleotide population.

As used herein, the term "polymerase" refers to a protein that is able to catalyze the specific incorporation of nucleotides to extend a 3' hydroxyl terminus of a primer molecule, such as, for example, the template oligonucleotide, against a nucleic acid target sequence. The polymerase can be, for example, thermophilic so that it is active at an elevated reaction temperature. It can also, for example, have strand displacement capabilities.

As used herein, the term "single nucleotide polymorphism (SNP)" refers to a DNA sequence variation occurring when a single nucleotide—A, T, C, or G—in the genome (or other shared sequence) differs between members of a species (or between paired chromosomes in an individual).

As used herein, the term "single nucleotide variant (SNV)" refers to one kind of genotype or polynucleotide including a single nucleotide polymorphism (SNP) or point mutation site.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a cancer.

As used herein, the terms "haplotype," "haploid genotype," and other grammatical equivalents herein refer to a set of nucleotide sequence polymorphisms or alleles present on a single maternal or paternal chromosome, usually inherited as a unit.

As used herein, the terms "phased sequencing," "haplotype sequencing," and other grammatical equivalents when used in context of a genome or a chromosome refer to determining the nucleic acid sequence of a single genome or single chromosome, respectively, where the nucleic acid sequence is obtained from the sequencing of a single genome or a single chromosome. The terms "phased sequencing," "haplotype sequencing," and other grammatical equivalents when used in context of a chromosomal fragment refer to determining the nucleic acid sequence of a single chromosomal fragment where the nucleic acid sequence is obtained from the sequencing of a single chromosomal fragment.

Methods for Amplifying Polynucleotides

Provided herein are methods for nuclease system mediated amplification, such as CRISPR-Cas mediated amplification and Argonaute mediated amplification.

In one aspect, the present disclosure provides a method for CRISPR-Cas system mediated amplification. In another aspect, the present disclosure provides a method for Argonaute medicated amplification. The methods provided herein is partially based on that binding of a guide nucleic acid such as a guide RNA or a guide DNA to a region of a target double-stranded nucleic acid disrupts the interaction between the two strands of the target nucleic acid, and thereby creates a loop structure (also called "R-loop") exposing the strand non-complementary to the guide nucleic acid. This exposed strand can be subjected to hybridization with primer for extension by an appropriate polymerase, e.g., in a nucleic acid amplification process. As illustrated in Example 1, this loop structure created by CRISPR-Cas systems, e.g., systems containing Cas9 or Cascade proteins, can be accessible to other enzymes. Thus, the loop structure can be further utilized as a template to initiate primer hybridization and interact with polymerase enzymes for amplification.

In some embodiments, the present disclosure provides a method for amplifying a target double-stranded nucleic acid including providing a system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; contacting the target double-stranded nucleic acid with the system to form a complex; hybridizing a primer to a second strand of the target double-stranded nucleic acid, the primer containing a sequence complementary to a region of the second strand of the target double-nucleic acid, and extending a nucleic acid complementary to the second strand of the target double-stranded nucleic acid from the primer using a polymerase.

In other embodiments, the present disclosure provides a method for amplifying a target double-stranded nucleic acid including providing a system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of a first strand of the target double-stranded nucleic acid; contacting the target double-stranded nucleic acid with the system to form a complex; hybridizing a primer to a second strand of the target double-stranded nucleic acid, the primer containing a sequence complementary to a region of the second strand of the target double-stranded nucleic acid, and extending a nucleic acid complementary to the second strand of the target double-stranded nucleic acid from the primer using a polymerase.

The methods provided herein can be used in various amplification methods, including but not limited to, linear nucleic acid amplification and exponential nucleic acid amplification.

In some embodiments, the target nucleic acid is amplified linearly according to the methods provided herein. For example, in some embodiments, the method provided herein further includes repeating hybridizing a primer to the second strand of the target double-stranded nucleic acid, and extending a nucleic acid complementary to the second strand of the target double-stranded nucleic acid from the primer using a polymerase for one or more times, e.g., until a desired amount of amplification is achieved.

In other embodiments, the target nucleic acid is amplified exponentially. In exemplary exponential nucleic acid amplification, the product (i.e., amplicon) doubles with every reaction cycle. "Exponential amplification" is a non-linear amplification that results in exponential growth in the number of nucleic acid copies present. Typically, in an exponential amplification, primer extension (or copying) occurs from both ends of an amplicon. To ensure that the newly created strand has a primer binding sites at both ends, in an exponential amplification, the 3' end of the new synthesized nucleic acid contains the reverse complement of a primer, and the ends of the template are usually copied in each amplification cycle.

The cycle number of the reactions according to the present methods depends on the applications and the desired amount of the amplification products. In some embodiments, cycle number is 5 to 100. In some embodiments, the cycle number is 10 to 90. In some embodiments, the cycle number is 20 to 80. In some embodiments, the cycle number is 30 to 70. In some embodiments, the cycle number is 40 to 60. Exemplary cycle number includes 10, 15, 20, 25, 30, 35, 40, 45, and 50. Cycles need not be synchronized between amplicons, as they are in a PCR reaction where the start of each cycle is controlled by changing the temperature. Cycles, as used herein, thus refers to the average number of rounds of amplification an amplicon undergoes.

In some embodiments, the initialization step includes provides multiple CRISPR-Cas systems or multiple Argonaute systems to the target nucleic acid to open the double-stranded nucleic acid structure at two or more targeted sequences and to form two or more R-Loop structures. The initialization step does not require heating the reaction, as required in a PCR reaction, because this initialization step is enzyme driven. The next step according to the present methods involves providing and annealing primers targeted to the R-Loop regions to form relatively stable nucleic acid-nucleic acid interaction, e.g., DNA-DNA hybrids. Typically, stable nucleic acid-nucleic acid hybrids are formed when the primer sequence has substantial complementarity the template sequence. Then one or more polymerases bind to the primer-template hybrid and begin nucleic acid synthesis in an extension/elongation step. In some embodiments, the temperature at this extension/elgation step depends on the polymerase used. At this step the polymerase synthesizes a new nucleic acid strand complementary to the template strand by adding dNTPs that are complementary to the template. In some embodiments, when DNA polymerase is used, the reaction condenses the 5'-phosphate group of the dNTPs with the 3'-hydroxyl group at the end of the nascent (extending) DNA strand. The extension time depends both on the polymerase used and on the length of the nucleic acid fragment to be amplified. One or more of these steps can be repeated for one or more times, e.g., until a desired amount of amplification is achieved.

To permit exponential growth of the amplified products, it is beneficial that the newly created nucleic acid product in each cycle contains primer binding sites at both ends. In some embodiments, the 3' end of the newly synthesized molecule is the reverse complement of a primer. In some embodiments, two primers, each targeting to one end of a target nucleic acid, can be used in an exponential amplification. In some embodiments, it is also beneficial that the primer is designed in such way that it can be targeted by the CRISPR-Cas systems provided herein—that is the primer can be targeted by the guide RNA, e.g., crRNA, of the CRISPR-Cas systems so that the CRISPR-Cas systems can be repeatedly used to bind to the target nucleic acid to initiate a new round of amplification. Similarly, in some embodiments, it is also beneficial that the primer is designed in such way that it can be targeted by the Argonaute systems provided herein—that is the primer can be targeted by the 5' phosphorylated single-stranded nucleic acid (guide nucleic acid), e.g., gDNA, of the Argonaute systems so that the Argonaute systems can be repeatedly used to bind to the target nucleic acid to initiate a new round of amplification.

Thus, in some embodiments, two or more CRISPR-Cas systems or Argonaute systems are used to initiate primer binding at both ends of a target nucleic acid.

In some embodiments, provided herein is a method for amplifying a target double-stranded nucleic acid including: (a) providing a first system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a target-specific nucleotide region complementary to a region of a first strand of the target double-stranded nucleic acid; (b) providing second system having: a second clustered regularly interspaced short palindromic repeats (CRISPR) RNA (crRNA)

or a derivative thereof, and a second CRISPR-associated (Cas) protein or a variant thereof, wherein the second crRNA or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, primer hybridization and extension by polymerase steps are repeated for one or more times, e.g., until a desired degree of amplification is reached.

In other embodiments, provided herein is a method for amplifying a target double-stranded nucleic acid comprising: (a) providing a first system having: a 5' phosphorylated single-stranded nucleic acid or a derivative thereof, and a first Argonaute protein or a variant thereof, wherein the first 5' phosphorylated single-stranded nucleic acid or the derivative thereof contains a target-specific nucleotide region complementary to a region of a first strand of the target double-stranded nucleic acid; (b) providing second system having: a second 5' phosphorylated single-stranded nucleic acid or a derivative thereof, and a second Argonaute protein or a variant thereof, wherein the second 5' phosphorylated single-stranded nucleic acid or the derivative thereof contains a target-specific nucleotide region complementary to a region of a second strand of the target double-stranded nucleic acid; (c) contacting the target double-stranded nucleic acid with the first system and the second system; (d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid. In some embodiments, the method provided herein further includes repeating step (a) and step (e) for one or more times, e.g., until a desired degree of amplification is reached.

In other embodiments, the method provided herein is used for multiplex amplification. As used herein, the term "multiplex amplification" refers to the amplification of more than one nucleic acid of interest, e.g., an amplification of multiple sequences from the same sample. The term "multiplex amplification" also refers to the amplification of one or more sequences present in multiple samples either simultaneously or in step-wise fashion. Thus, in some embodiments, two or more target nucleic acid sequences are being amplified in an amplification reaction, and the amplification reaction comprises the appropriate templates and enzymes to amplify at least two target nucleic acid sequences. One application of the multiplex amplification provided herein is to detect two or more target sequences in a sample because multiplex amplification is cable of amplifying two or more target sequences. When only one of the target sequences is actually present in the sample being tested, the result of the multiplex amplification can be amplification of the only one sequence that is present. Multiplex amplification may utilize the same primer pairs to amplify a one or more intervening amplicon sequences. Alternatively, multiplex amplification may utilized one or more primer pairs.

In some embodiments, the double-stranded nucleic acid provided herein is a double-stranded DNA. In other embodiments, the double-stranded nucleic acid provided herein is a double-stranded RNA. In some embodiments, the target nucleic acid is genomic DNA. In other embodiments, the target nucleic acid contains chromosomal DNA or a fragment thereof. In yet other embodiments, the target nucleic acid comprises a genome or a partial genome.

In some embodiments, the systems provided herein are derived from CRISPR-Cas systems. CRISPR-Cas systems can generally be categorized into three major types (Type I-III), which are further subdivided into ten subtypes, based on core element content and sequences (Makarova et al., 2011, *Nat Rev Microbiol* 9:467-77). The two key elements of these CRISPR-Cas systems are Cas proteins and CRISPR RNA (crRNA). crRNA consists of short repeat sequences interspersed with spacer sequences derived from invader DNA. Cas proteins have various activities, e.g., nuclease activity. Thus, CRISPR-Cas systems provide mechanisms for targeting a specific sequence as well as certain enzyme activities upon the sequence.

A typical Type I CRISPR-Cas system contains Cas3 protein with separate helicase and DNase activities. For example, in the Type 1-E system, crRNAs are incorporated into a multisubunit effector complex called Cascade (CRISPR-associated complex for antiviral defense) (Brouns et al., 2008, *Science* 321: 960-4), which binds to the target DNA and triggers degradation by the Cas3 protein (Sinkunas et al., 2011, *EMBO J* 30:1335-1342; Beloglazova et al., 2011, *EMBO J* 30:616-627).

Type II CRISPR-Cas systems include the signature Cas9 protein, a single protein (about 160 KDa), capable of generating crRNA and cleaving the target DNA. The Cas9 protein typically contains two nuclease domains, a RuvC-like nuclease domain near the amino terminus and the HNH (or McrA-like) nuclease domain near the middle of the protein. Each nuclease domain of the Cas9 protein is specialized for cutting one strand of the double helix (Jinek et al., 2012, *Science* 337 (6096): 816-821).

Type III CRISPR-Cas systems contain polymerase and RAMP modules. Type III systems can be further divided into sub-types III-A and III-B. Type III-A CRISPR-Cas systems have been shown to target plasmids, and the polymerase-like proteins of Type III-A systems are involved in the cleavage of target DNA (Marraffini and Sontheimer, 2008, *Science* 322:1843-1845). Type III-B CRISPR-Cas systems have also been shown to target RNA (Hale et al., 2009, *Cell* 139:945-956).

Thus, in some embodiments, the system is a Type I CRISPR-Cas system or a derivative thereof. In other embodiments, the system is a Type II CRISPR-Cas system or a derivative thereof. In yet other embodiments, the system is a Type III CRISPR-Cas system or a derivative thereof.

The key elements of a CRISPR-Cas system include a guide RNA, e.g., a crRNA, and a Cas protein. The crRNA or the derivative thereof contains a target specific nucleotide region complementary or substantially complementary to a region of the target nucleic acid. In some embodiments, the crRNA or the derivative thereof contains a user-selectable RNA sequence that permits specific targeting of the enzyme to a complementary double-stranded DNA. In some embodiments, the user-selectable RNA sequence contains 20-50 nucleotides complementary or substantially complementary to a region of the target DNA sequence. In some embodiments, the user-selectable RNA sequence contains less than 20 nucleotides complementary or substantially complementary to a region of the target DNA sequence. Exemplary user-selectable RNA sequence contains 1, 2, 3, 4, 5, 6, 7, 8, 9, 10, 11, 12, 13, 14, 15, 16, 17, 18, or 19 nucelotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the crRNA and the region of the target nucleic acid. In some embodiments, there are three base pair mismatches between the target specific nucleotide region of the crRNA and the region of the target nucleic acid. In some embodiments, there are four base pair mismatches between the target specific nucleotide region of the crRNA and the region of the target nucleic acid. In some embodiments, there are five base pair mismatches between the target specific nucleotide region of the crRNA and the region of the target nucleic acid.

In some embodiments, the system provided herein further includes a trans-activating crRNA (tracrRNA) or a derivative thereof.

The CRISPR-Cas systems provided herein include engineered and/or programmed nuclease systems derived from naturally occurring CRISPR-Cas systems. CRISPR-Cas systems may include contain engineered and/or mutated Cas proteins. CRISPR-Cas systems may also contain engineered and/or programmed guide RNA. In some embodiments, the crRNA or the derivative thereof provided herein is a polynucleotide having a crRNA polynucleotide fused to a tracrRNA polynucleotide. A chimeric single-guided RNA (sgRNA) is described in Jinek et al., 2012, *Science* 337, 816-821, which is incorporated herein in its entirety. In one embodiment, the Cas protein or the variant thereof provided herein can be directed by a chimeric sgRNA to any genomic locus followed by a 5'-NGG protospacer-adjacent motif (PAM). For example, in some embodiments, crRNA and tracrRNA are synthesized by in vitro transcription, using a synthetic double stranded DNA template containing the T7 promoter. The tracrRNA has a fixed sequence, whereas the target sequence dictates part of crRNA's sequence. Equal molarities of crRNA and tracrRNA are mixed and heated at 55° C. for 30 seconds. Cas9 is added at the same molarity at 37° C. and incubated for 10 minutes with the RNA mix. 10-20 fold molar excess of Cas9 complex is then added to the target DNA. The binding reaction can occur within 15 minutes.

In some embodiments, the Cas protein or the variant thereof is a Cas9 protein or a variant thereof. Isolated Cas9-crRNA complex from the *S. thermophilus* CRISPR-Cas system as well as complex assembled in vitro from separate components demonstrate that it binds to both synthetic oligodeoxynucleotide and plasmid DNA bearing a nucleotide sequence complementary to the crRNA. It has been shown that Cas9 has two nuclease domains—RuvC- and HNH-active sites/nuclease domains, and these two nuclease domains are responsible for the cleavage of opposite DNA strands. In some embodiments, the Cas9 protein is derived from Cas9 protein of *S. thermophilus* CRISPR-Cas system. In some embodiments, the Cas9 protein is a multi-domain protein having about 1,409 amino acids residues.

In some embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In some embodiments, the Cas protein or the variant thereof is a Cascade protein or a variant thereof. Cascade complex in *E. coli* recognizes double-stranded DNA (dsDNA) targets in a sequence-specific manner. *E. coli* Cascade complex is a 405-kDa complex comprising five functionally essential CRISPR-associated (Cas) proteins (CasA1B2C6D1E1, also called Cascade protein) and a 61-nucleotide crRNA. The crRNA guides Cascade complex to dsDNA target sequences by forming base pairs with the complementary DNA strand while displacing the non-complementary strand to form an R-loop. Cascade recognizes target DNA without consuming ATP, which suggests that continuous invader DNA surveillance takes place without energy investment. Matthijs et al., Nature Structural & Molecular Biology, 2011, 18, 529-536.

In some embodiments, the Cas protein or the variant thereof is a Cas3 protein or a variant thereof. *E. coli* Cas3 can catalyse ATP-independent annealing of RNA with DNA forming R-loops, and hybrid of RNA base-paired into duplex DNA. Cas3 protein can use gRNA that is longer than that for Cas9. Howard et al., Biochem J., 2011, 439(1):85-95. Such longer RNA can permit easier access of other elements to the target DNA, e.g., access of a primer to be extended by polymerase. Another advantage provided by Cas3 protein is that Cas3 protein does not require a PAM sequence as Cas9, thus provides more flexibility for targeting desired sequence. R-loop formation by Cas3 may require magnesium as a co-factor. Howard et al., Biochem J., 2011, 439(1):85-95. Thus, in some embodiments, the system provided herein further comprises magnesium.

It should be appreciated that any CRISPR-Cas systems capable of disrupting the double stranded nucleic acid and creating a loop structure can be used in the present methods. For example, the Cas proteins provided herein may include, but not limited to, the Cas proteins described in Haft et al., *PLoS Comput Biol.*, 2005, 1(6): e60, and Zhang et al., *Nucl. Acids Res.*, 2013, 10.1093/nar/gkt1262. Some these CRISPR-Cas systems require that a specific sequence be present for these CRISPR-Cas systems to recognize and bind to the target sequence. For instance, Cas9 requires the presence of a 5'-NGG protospacer-adjacent motif (PAM). Thus, in some embodiments, a PAM sequence or a sequence complementary to a PAM sequence is engineered into the target nucleic acid for initiating the binding of the CRISPR-Cas systems to the target nucleic acid.

In other embodiments, the systems provided herein are derived from Argonaute systems. Argonaute protein family was first discovered genetically, and was first identified in plants. Members are defined by the presence of PAZ (Piwi-Argonaute-Zwille) and PIWI domains. Argonaute proteins are highly conserved between species and many organisms encode multiple members of the family. Numbers of Argonaute genes range from 1 in the fission yeast *Schizosaccharomyces pombe* to 27 in the nematode worm *Caenorhabditis elegans*. In mammals there are eight Argonaute genes. The Argonaute protein family can be divided into the Ago subfamily and the Piwi subfamily. In most organisms investigated so far, which include *Drosophila*, the zebrafish and the mouse, the expression of Piwi proteins is restricted to the germ line, where they bind Piwi-interacting proteins (piR-NAs). In contrast, Ago proteins are ubiquitously expressed in many organisms. Human Ago1, Ago3 and Ago4 genes are clustered on chromosome 1, whereas the Ago2 gene is located on chromosome 8. The human Piwi subfamily comprises HIWI1, HIWI2, HIWI3 and HILI; they are encoded by genes on chromosomes 12, 11, 22 and 8, respectively. It was shown that members of the Argonaute protein family are key players in gene-silencing pathways guided by small RNAs. Small RNAs such as short interfering RNAs (siRNAs), microRNAs (miRNAs) or Piwi-interacting RNAs (piRNAs) are anchored into specific binding pockets and guide Argonaute proteins to target mRNA molecules for silencing or destruction. Hock and Meister, *Genome Biol.,* 2008, 9(2): 210. Recently, it was also shown that certain Argonaute proteins are guided by small DNA for performing DNA cleavage. See, e.g., Gao et al., *nature biotechnology,* 2016, doi: 10.1038/nbt.3547. Thus, Argonaute systems provide mechanisms for targeting a specific sequence as well as certain enzyme activities upon the sequence.

Thus, in some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

The key elements of an Argonaute system include a guide nucleic acid, e.g., 5' phosphorylated single-stranded nucleic acid. The 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucleotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

It should be appreciated that any Argonaute systems capable of binding to a nucleic acid through a guide nucleic acid, or disrupting the double stranded nucleic acid and creating a loop structure can be used in the present methods.

In some embodiments, the primer provided herein is a single-stranded oligodeoxyribonucleotide. In some embodiments, the length of a primer ranges from about 10 to about 50 nucleotides. Exemplary length of the primer provided herein is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

In some embodiments, the primer provided herein has 100% base pair matching with a region of the target nucleic acid. In some embodiments, the primer provided herein has 90%-100%, 80%-100%, or 70%-100% base pair matching with the region of the target nucleic acid. In some embodiments, there is one base pair mismatch between the primer and the region of the target nucleic acid. In some embodiments, there are two base pair mismatches between the primer and the region of the target nucleic acid. In some embodiments, there are three base pair mismatches between the primer and the region of the target nucleic acid. In some embodiments, there are four base pair mismatches between the primer and the region of the target nucleic acid. In some embodiments, there are five base pair mismatches between the primer and the region of the target nucleic acid.

In some embodiments, the primer provided herein is labeled, e.g., for enrichment or detection of the amplified products. In some embodiments, the primer provided herein is labeled for detection by spectroscopic, photochemical, biochemical, immunochemical, or chemical means. In some embodiments, the primer is labeled with biotin, amine, radiolabels (e.g., 32P), fluorescent dyes, electron-dense reagents, enzymes (as commonly used in ELISAS), or biotin.

In some embodiments, the polymerase provided herein catalyzes incorporation of nucleotides to extend a 3' hydroxyl terminus of a primer molecule against a nucleic acid target sequence. In some embodiments, the reaction by the polymerase provided herein is performed in isothermal conditions. In some embodiments, the polymerase is a strand-displacing polymerase. Exemplary polymerases include but not limited to Bst DNA polymerase, 9° Nm DNA polymerase, Phi29 DNA polymerase, DNA polymerase I (*E. coli*), DNA polymerase I (Large)m, (Klenow) fragment, Klenow fragment (3'-5' exo-), T4 DNA polymerase, T7 DNA polymerase, Deep VentR™ (exo-) DNA polymerase, Deep VentR™ DNA polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo-) DNA Polymerase, RepliPHI™ Phi29 DNA Polymerase, rBst DNA Polymerase, rBst DNA Polymerase (Large), Fragment (IsoTherm™ DNA Polymerase), MasterAmp™ AmpliTherm™, DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, and Thermo-Phi DNA polymerase. In some embodiments, the polymerase is selected from a group consisting of Bst, Bsu, and Phi29. As the polymerase extends the hybridized strand, it can be beneficial to include single-stranded binding protein (SSB). SSB may stabilize the displaced (non-template) strand. Thus, in some embodiments, the method provided herein can further include SSB protein.

As discussed, one advantage provided by the linear or exponential amplifications provided herein is that the amplifications can be performed under constant temperature or isothermal conditions. As used herein, the term "constant temperature," "isothermal conditions," or "isothermally" refers to a set of reaction conditions where the temperature of the reaction is kept essentially constant during the course of the amplification reaction. However, it is not necessary that the temperature be maintained at precisely one temperature. If the equipment used to maintain an elevated temperature allows the temperature of the reaction mixture to vary by a few degrees, this is not detrimental to the amplification reaction, and can still be considered to be an isothermal reaction. In some embodiments, the amplification reaction is run at a constant temperature between 20° C. to 70° C. In some embodiments, the amplification reaction is run at a constant temperature between 25° C. to 60° C. In some embodiments, the amplification reaction is run at a constant temperature between 40° C. to 55° C. In some embodiments, the amplification reaction is run at a constant temperature between 30° C. to 40° C. Exemplary amplification reaction temperatures include 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., and 60° C. In one embodiment, the amplification reaction temperature is about 37° C.

In some embodiments, the time that the amplification reaction is run may vary from, for example, 1 minute to several hours until the desired amount of the amplification is achieved. In some embodiments, the time that the amplification reaction is 5 minutes to 1 hour. Exemplary times of the amplification reaction include 5 minutes, 10 minutes, 15 minutes, 20 minutes, 30 minutes, 40 minutes, 50 minutes, and 60 minutes.

In some embodiments, the present methods can be used in certain applications wherein detection and/or quantification of the amplified nucleic acid products are desired. The amplified target sequence can be detected by any method known to one of ordinary skill in the art.

In some embodiments, dyes that specifically stain double-stranded DNA can be used to detect or quantify the amplified products. In some embodiments, intercalating dyes exhibit enhanced fluorescence upon binding to DNA or RNA. In some embodiments, dyes can be, for example, DNA or RNA intercalating fluorophores. Exemplary DNA or RNA intercalating fluorophores include but are not limited to Acridine orange, ethidium bromide, Hoechst dyes, PicoGreen, propidium iodide, SYBR I (an asymmetrical cyanine dye), SYBR II, TOTO (a thiaxole orange dimer) and YOYO (an oxazole yellow dimer).

In some embodiments, amplified products with specific sizes can be detected by gel electrophoresis. In some embodiments, the nucleotides used in the amplification reaction, can be labeled, e.g., with biotin. Biotin-labeled amplified sequences can be captured using avidin bound to a signal generating enzyme, for example, peroxidase.

In some embodiments, labeled nucleotides can be incorporated directly into the target sequence or into primers containing complementary sequences to the target of interested. Such labels can be radioactive and/or fluorescent in nature and can be resolved in any of the manners discussed herein.

Methods of detecting and/or continuously monitoring the amplification of nucleic acid products are also well known to those skilled in the art. For example, in some embodiments, the production or presence of target nucleic acids and nucleic acid sequences may be detected and monitored by Molecular Beacons. Molecular Beacons are hairpin shaped oligonucleotides containing a fluorophore on one end and a quenching dye on the opposite end. The loop of the hair-pin contains a probe sequence that is complementary to a target sequence and the stem is formed by annealing of complementary arm sequences located on either side of the probe sequence. When the molecular beacon encounters a target molecule, hybridization occurs; the loop structure is converted to a stable more rigid conformation causing separation of the fluorophore and quencher molecules leading to fluorescence. Tyagi et al., Nature Biotechnology, 1996, 303-308. Thus, the generation of fluorescence indicates the synthesis of the intended amplified product. For another example, in some embodiments, the production or presence of target nucleic acids and nucleic acid sequences can be detected and monitored by Fluorescence resonance energy transfer (FRET). FRET is a useful tool to quantify molecular dynamics, for example, in DNA-DNA interactions. For monitoring the production of a specific product a probe can be labeled with a donor molecule on one end and an acceptor molecule on the other. Probe-target hybridization brings a change in the distance or orientation of the donor and acceptor and FRET change is observed. Lakowicz, "Principles of Fluorescence Spectroscopy," Plenum Publishing Corporation, 2nd edition (Jul. 1, 1999). Other exemplary methods for detecting and/or continuously monitoring the amplification of nucleic acid products include but not limited to Mass Spectrometry, capillary gel electrophoresis, sequencing, and various surface capture methods as known to those skilled in the art. In some embodiments, running the amplification reaction with asymmetric amounts of primers, i.e., with one primer present in higher concentration than the other, would permit amplification with a bias towards one strand. An excess of a single strand may facilitate detection by such modalities as Molecular Beacons, which detect ssDNA.

The amplification methods provided herein can be used in various applications. For example, in some embodiments, the method provided herein can be used to isolate DNA fragments from genomic DNA by selective amplification of a specific region of DNA.

For another example, in some embodiments, the amplification methods provided herein can be used for diagnosing various diseases based on the production or presence of a target nucleic acid linked to a specific disease. In some embodiments, the methods provided herein can be used for early diagnosis of malignant diseases, e.g., leukemia and lymphomas. In other embodiments, methods provided herein can be used directly on genomic DNA samples to amplify and detect translocation-specific malignant cells.

In other embodiments, the methods provided herein can be used for diagnosis of infectious diseases, including those caused by bacteria or viruses. For example, the present methods can be used to detect infectious agents and distinguish non-pathogenic from pathogenic strains by virtue of specific nucleic acid sequence. In some embodiments, the amplification methods provided herein can amplify and identify non-cultivatable or slow-growing microorganisms, e.g., mycobacteria, anaerobic bacteria, or viruses from tissue culture assays and animal models. In other embodiments, the amplification methods provided herein can amplify and identify viral DNA in a sample from an individual.

In yet other embodiments, the present amplification methods can be used to generate nucleic acid materials to augment other procedures. For example, in some embodiments, the present amplification methods can be used for generating hybridization probes for Southern or northern hybridization and DNA cloning, which require relatively larger amounts of DNA, representing a specific DNA region. For another example, the methods provided herein can be used for nucleic acid sequencing.

In a specific embodiment, the CRISPR-Cas or Argonaute mediated nucleic acid amplification methods provided herein can be used for amplifying a library of nucleic acid fragments, e.g., generated using library preparation methods and/or kits available from Illumina, Inc. (San Diego, Calif.).

In some embodiments, the methods provided herein can be used to amplify a library of nucleic acid fragments generated from genomic DNA. In a specific embodiment, the library of nucleic acid fragments is generated using tagmentation. In a specific embodiment, the library of nucleic acid fragments is generated from genomic DNA using Illumina's Nextera library preparation methods and kits (available from Illumina, Inc, San Diego, Calif.).

Thus, in some embodiments, the method provided herein further includes applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments, and thus incorporates a universal primer sequence into each of the plurality of target nucleic acid fragments, wherein the guide nucleic acid in the nuclease system, such a crRNA or the derivative thereof or a 5' phosphorylated single-stranded nucleic acid, contains a target-specific nucleotide region complementary to a region of the universal primer.

In some embodiments, the target nucleic acid is subjected to a transposase mediated tagmentation that results in fragmentation of the target nucleic acid and ligation of adaptors to the 5' end of both strands of double-stranded DNA fragments. Optionally, the target nucleic acid can be fragmented and adaptors can be added to the 5' and 3' ends using tagmentation or transposition as described in U.S. Publication No. 2010/0120098, which is incorporated by reference herein in its entirety. Briefly, a transposition reaction is a reaction wherein one or more transposons are inserted into target nucleic acids at random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. Exemplary transposition complexes, suitable for use in the methods provided herein, include, but are not limited to, those formed by a hyperactive Tn5 transposase and a Tn5-type transposon end or by a MuA transposase and a Mu transposon end comprising R1 and R2 end sequences (see, e.g., Goryshin and Reznikoff, *J. Biol. Chem.* 273: 7367, 1998; and Mizuuchi, *Cell* 35: 785, 1983; Savilahti et al., *EMBO J.* 14: 4893, 1995; which are incorporated by reference herein in their entireties). However, any transposition system that is capable of inserting a transposon end with sufficient efficiency to tag target nucleic acids for its intended purpose can be used in the provided methods. Other examples of known transposition systems that could be used in the provided methods include, but are not limited to, *Staphylococcus aureus* Tn552, Ty1, Transposon Tn7, Tn/O and IS10, Mariner transposase, Tc1, P Element, Tn3, bacterial insertion sequences, retroviruses, and retrotransposon of yeast (see, e.g., Colegio et al., 2001, *J. Bacteriol.* 183: 2384-8; kirby et al., 2002, *Mol. Microbiol.* 43: 173-86; Devine and Boeke, 1994, *Nucleic Acids Res.*, 22: 3765-72; International Patent Application No. WO 95/23875; Craig, 1996, *Science* 271: 1512; Craig, 1996, Review in: *Curr Top Microbiol Immunol.* 204: 27-48; Kleckner et al., 1996, *Curr Top Microbiol Immunol.* 204: 49-82; Lampe et al., 1996, *EMBO J.* 15: 5470-9; Plasterk, 1996, *Curr Top Microbiol Immunol* 204: 125-43; Gloor, 2004, *Methods Mol. Biol.* 260: 97-114; Ichikawa and Ohtsubo, 1990, *J Biol. Chem.* 265: 18829-32; Ohtsubo and Sekine, 1996, *Curr. Top. Microbiol. Immunol.* 204: 1-26; Brown et al., 1989, *Proc Natl Acad Sci USA* 86: 2525-9; Boeke and Corces, 1989, *Annu Rev Microbiol.* 43: 403-34; which are incorporated herein by reference in their entireties). In some embodiments, the method of the present disclosure further comprises removing the transposase enzyme and adding to the ends of the adapted DNA fragments by PCR.

The term "tagmentation," "tagment," or "tagmenting," as used herein, refers to transforming a nucleic acid, e.g., a DNA, into adaptor-modified templates in solution ready for cluster formation and sequencing by the use of transposase mediated fragmentation and tagging. This process often involves the modification of the nucleic acid by a transposome complex comprising transposase enzyme complexed with adaptors comprising transposon end sequence. Tagmentation results in the simultaneous fragmentation of the nucleic acid and ligation of the adaptors to the 5' ends of both strands of duplex fragments. Following a purification step to remove the transposase enzyme, additional sequences are added to the ends of the adapted fragments by PCR.

The term "transposome complex," as used herein, refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in the present invention. In particular embodiments, a preferred transposition system is capable of inserting the transposon end in a random or in an almost random manner to 5'-tag and fragment the target nucleic acid.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further comprise additional sequences (e.g., adaptor or primer sequences) as needed or desired. In some embodiments, the method provided herein is exemplified by employing a transposition complex formed by a hyperactive Tn5 transposase and a Tn5-type transposon end (Goryshin and Reznikoff, 1998, *J. Biol. Chem.*, 273: 7367) or by a MuA transposase and a Mu transposon end comprising R1 and R2 end sequences (Mizuuchi, 1983, *Cell*, 35: 785; Savilahti et al., 1995, *EMBO J.*, 14: 4893). However, any transposition system that is capable of inserting a transposon end in a random or in an almost random manner with sufficient efficiency to 5'-tag and fragment a target DNA for its intended purpose can be used in the present invention. Examples of transposition systems known in the art which can be used for the present methods include but are not limited to *Staphylococcus aureus* Tn552 (Colegio et al., 2001, *J Bacteriol.*, 183: 2384-8; Kirby et al., 2002, *Mol Microbiol*, 43: 173-86), Ty1 (Devine and Boeke, 1994, *Nucleic Acids Res.*, 22: 3765-72 and International Patent Application No. WO 95/23875), Transposon Tn7 (Craig, 1996, *Science*. 271: 1512; Craig, 1996, Review in: *Curr Top Microbiol Immunol*, 204: 27-48), Tn10 and IS10 (Kleckner et al., 1996, *Curr Top Microbiol Immunol*, 204: 49-82), Mariner transposase (Lampe et al., 1996, *EMBO J.*, 15: 5470-9), Tci (Plasterk, 1996, *Curr Top Microbiol Immunol*, 204: 125-43), P Element (Gloor, 2004, *Methods Mol Biol*, 260: 97-114), TnJ (Ichikawa and Ohtsubo, 1990, *J Biol Chem*. 265: 18829-32), bacterial insertion sequences (Ohtsubo and Sekine, 1996, *Curr. Top. Microbiol. Immunol.* 204:1-26), retroviruses (Brown et al., 1989, *Proc Natl Acad Sci USA*, 86: 2525-9), and retrotransposon of yeast (Boeke and Corces, 1989, *Annu Rev Microbiol.* 43: 403-34). The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase.

The term "transposon end" (TE) refers to a double-stranded nucleic acid, e.g., a double-stranded DNA, that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is sometimes used in the present disclosure in connection with the composition of transposon ends, it should be understood that any suitable nucleic acid or nucleic acid analogue can be utilized in a transposon end.

Through an in vitro transposition reaction, target nucleic acid fragments are tagged at the 5' end. In some embodiments, the method provided herein further includes steps to incorporate a 3' end tag to the 5' tagged nucleic acid fragments to make a library of di-tagged nucleic acid fragments. Adding 3' end tag can be performed through various methods, e.g., by using DNA polymerase, terminal transferase, and/or ligase as described in WO 2010/048605 the content of which is incorporated by its entirety.

In some embodiments, di-tagged nucleic acid fragments are generated by using a polymerase, e.g., a DNA polymerase, with strand-displacement or 5' nuclease activity. In some embodiments, the method provided herein includes incubating the population of annealed 5'-tagged nucleic acid fragments with a DNA polymerase that has strand-displacement or 5' nuclease activity under conditions without thermocycling and wherein the annealed 5'-tagged nucleic acid fragments are not denatured, wherein the DNA polymerase extends the 3'-end of each strand of the annealed 5'-tagged nucleic acid fragments using the complementary strand as a template and displaces or digests the non-transferred strand, thereby generating the library of di-tagged double-stranded DNA fragments.

In other embodiments, the 5'-tagged nucleic acid fragments are incubated with a DNA polymerase consisting of a terminal transferase and at least one substrate for the terminal transferase under conditions and for sufficient time wherein the terminal transferase joins the second tag to the 3' end of the 5'-tagged nucleic acid fragments, thereby generating a library of di-tagged nucleic acid fragments. In some embodiments, the 3'-end of the non-transferred transposon end that composes the transposon end composition is blocked (e.g., by using a non-transferred transposon end that has a dideoxy nucleotide or a 3'-O-methyl-nucleotide as the 3'-terminal nucleotide).

In yet other embodiments, di-tagged nucleic acid fragments are generated by using a template-dependent ligase and a ligation tagging oligonucleotide. In some embodiments, the 5'-tagged nucleic acid fragments are incubated with a template-dependent DNA ligase and a ligation tagging oligodeoxynucleotide having a 3'-portion and a 5'-portion, wherein the 3'-portion exhibits a second tag that exhibits any sequence that is desired to be joined to the 3'-end of the 5'-tagged DNA fragments and the 5'-portion has a 5'-monophosphate group and exhibits a random sequence, under conditions and for sufficient time wherein the second tag is joined to the annealed 5'-tagged DNA fragments, thereby generating a library of DNA fragments comprising annealed di-tagged DNA fragments.

In some embodiments, the nucleic acid fragments generated contain universal sequences at the two ends of the nucleic acid fragments. The universal sequences at the two ends of the nucleic acid fragments, e.g., in a library, can be targeted to by the CRISPR-Cas system or the Argonaute system according the methods provided herein, and as such the fragments can be amplified, e.g., in a cluster formation reaction.

Such universal sequences can be introduced into the two ends of the nucleic acid fragments in a library by a PCR or Nextera transposon reaction. In some embodiments, after a library of tagged nucleic acid fragments is generated, the tagged nucleic acid fragments can be amplified, e.g., using limited-cycle polymerase chain reaction (PCR), to introduce other end sequences or adaptors, e.g., index, universal primers and other sequences required for cluster formation and sequencing. In a specific embodiment, a limited-cycle PCR amplification is performed to add index 1 (P7) and index 2 (P5) (available from Illumina, Inc, San Diego, Calif.) to the two ends of the nucleic acid fragments.

In some embodiments, such amplification is performed to a library of 5' tagged nucleic acid fragments. In some embodiments, such amplification is performed to a library of di-tagged nucleic acid fragments. Exemplary amplification methods include polymerase chain reaction (PCR), strand-displacement amplification reaction, rolling circle amplification reaction, ligase chain reaction, transcription-mediated amplification reaction, and loop-mediated amplification reaction.

In some embodiments, the method provided herein includes amplifying the library of di-tagged nucleic acid fragments using a PCR. In some embodiments, provided herein includes amplifying the library of di-tagged nucleic acid fragments using the Cas9 or Argonaute mediated amplification method provided herein. In some embodiments, the method provided herein uses single-primer PCR amplification of a library of di-tagged DNA fragments. In some embodiments, the step of amplifying di-tagged DNA fragments includes using a DNA polymerase and at least one primer that is complementary to the second tag. In some embodiments, the step of amplifying the library of di-tagged DNA fragments includes amplifying the library of tagged DNA fragments by PCR using only one oligodeoxyribonucleotide that exhibits the sequence of at least a portion of the transferred strand as a PCR primer and the di-tagged DNA fragments as templates. In some embodiments, the primer contains a 5' portion that contains additional sequence, e.g., an adaptor sequence.

In some embodiments, two different PCR primers are used, each of which PCR primers exhibits the sequence of at least a portion of the transferred transposon end that composes the transposon end composition. In some embodiments, each PCR primer includes a 3'-portion and a 5'-portion, wherein the 3'-portion exhibits the respective transferred transposon end sequence and the 5'-portion exhibits the sequence of a respective tag domain or an adaptor for a particular purpose (e.g., a sequencing tag domain/adaptor or an amplification tag domain/adaptor, and optionally an address tag domain/adaptor for next-generation sequencing or amplification). For example, when a single transposon end composition is used in the in vitro transposition reaction to generate the library of di-tagged DNA fragments using a DNA polymerase that has strand-displacement or 5' nuclease activity, the di-tagged DNA fragments can be amplified by PCR using two different PCR primers. Each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain/adaptor or an amplification tag domain/adaptor, and optionally an address tag domain/adaptor for next-generation sequencing or amplification). In some embodiments, the 5' portion of each PCR primer is different from that of the other primer, and as such the sequences of the two ends of the PCR product are different. For example, one end contains one index and/or universal primer sequence, and the other end contains a different index and/or universal primer sequence.

In some embodiments, the two ends of di-tagged nucleic acid fragments originate from two different transferred strand sequences. For example, in some embodiments, two different transposomes can be used in the in vitro transposition reaction, and each of the two transposomes contains the same transposase but a different transposon end composition. In some embodiments, two different transposomes are used, and the two different transposomes each contains the same transposase and the transposon end compositions contain different transferred strands. In some embodiments, two different transposomes are used, and each of the two transposomes includes different transposase enzymes and different transposon end compositions, each of which forms a functional complex with the respective transposase. In some embodiments, wherein two different transposon end compositions are used in the in vitro transposition reaction, and the library of di-tagged single stranded nucleic acid fragments is generated using a DNA polymerase that has strand-displacement or 5' nuclease activity, the first tag exhibits the sequence of the transferred strand of one transposon end composition and the second tag exhibits the sequence of the non-transferred strand of the other transposon end composition.

In the above mentioned embodiments and other embodiments wherein two different transferred strands are linked to the 5' end of each opposite strands of the double stranded nucleic acid, the method provided herein can further include the step of amplifying the di-tagged nucleic acid fragments by PCR using two different PCR primers. One of the PCR primers exhibits the sequence of at least a portion of one transferred strand that compose one transposon end composition, and the other of PCR primers exhibits the sequence of at least a portion of the other transferred strand that composes the other transposon end composition.

In some embodiments wherein two primers are used, each PCR primer contains a 3'-portion and a 5'-portion, wherein the 3'-portion exhibits the respective transferred transposon end sequence and the 5'-portion exhibits the sequence of a respective tag domain/adaptor for a particular purpose (e.g., a sequencing tag domain or an amplification tag domain, and optionally an address tag domain for next-generation sequencing or amplification). In some embodiments, the 5' portion of each PCR primer is different from that of the other primer, and as such to introduce different sequences to the two ends of the PCR product. In some embodiments, the 5' portion of the first PCR primer or the 5' portion of the second PCR primer, or the 5' portions of both the first and the second PCR primers contain first or second sequencing tags/adaptors, respectively, for generation of templates for next-generation sequencing for a particular sequencing platform (e.g., sequencing tags for an Illumina Nextera sequencing platform). In some embodiments, the 5' portion of the first PCR primer or the 5' portion of the second PCR primer additionally contains an address tag domain/adaptor or another tag domain/adaptor for a particular purpose.

A wide variety of enzymes and kits are available for performing the amplification reaction by PCR as known by those skilled in the art. For example, in some embodiments, the PCR amplification is performed using either the FAIL-SAFE™ PCR System or the MASTERAMP™ Extra-Long PCR System from EPICENTRE Biotechnologies, Madison, Wis., as described by the manufacturer. However, the present disclosure is not limited to the use of those products or conditions for the amplification reaction and any suitable thermostable DNA polymerase and reaction mixture that permits amplification of the sequence between the primer that anneals to the target sequence and the primer that anneals to the transposon can be used.

The method provide herein is not limited to the use of PCR to amplify the library of tagged nucleic acid fragments. Any suitable amplification method (e.g., rolling circle amplification, riboprimer amplification (e.g., U.S. Pat. No. 7,413,857), ICAN, UCAN, ribospia, terminal tagging (U.S. Patent Application No. 20050153333), Eberwine-type aRNA amplification or strand-displacement amplification) that amplifies the same sequence, and generates a suitable composition and amount of amplification product for the intended purpose can be used in embodiments of the present invention. For example, some strand displacement methods that can be used are described in PCT Patent Publication Nos. WO 02/16639; WO 00/56877; and AU 00/29742; of Takara Shuzo Company, Kyoto, Japan; U.S. Pat. Nos. 5,523,204; 5,536,649; 5,624,825; 5,631,147; 5,648,211; 5,733,752; 5,744,311; 5,756,702; and 5,916,779 of Becton Dickinson and Company; U.S. Pat. Nos. 6,238,868; 6,309,833; and 6,326,173 of Nanogen/Becton Dickinson Partnership; U.S. Pat. Nos. 5,849,547; 5,874,260; and 6,218,151 of Bio Merieux; U.S. Pat. Nos. 5,786,183; 6,087,133; and 6,214,587 of Gen-Probe, Inc.; U.S. Pat. No. 6,063,604 of Wick et al; U.S. Pat. No. 6,251,639 of Kurn; U.S. Pat. No. 6,410,278; and PCT Publication No. WO 00/28082 of Eiken Kagaku Kabushiki Kaishi, Tokyo, Japan; U.S. Pat. Nos. 5,591,609; 5,614,389; 5,773,733; 5,834,202; and 6,448,017 of Auerbach; and U.S. Pat. Nos. 6,124,120; and 6,280,949 of Lizardi. In some embodiments, Cas mediated amplification provided herein is used to amplify the library of the target nucleic acid fragments.

In some embodiments, when the target nucleic acid has a universal primer sequence, e.g., as generated using the methods provided above, a guide RNA, e.g., a crRNA, can target to the universal primer sequence of the nucleic acid fragments in the library so that to amplify the library of nucleic acid fragments isothermally.

FIG. 1 illustrates a method to amplify nucleic acid fragments generated by Nextera library preparation (available from Illumina, Inc., San Diego, Calif.) according to the present disclosure. In some embodiments, the Cas proteins provided herein require a PAM sequence in order to recognize a target. For example, Cas9 protein requires a sequence of the motif NGG residing adjacent to the target sequence. A sequence complementary to the PAM sequence can be incorporated into the flowcell primers (e.g., P5 and P7) that are added to library inserts to result in PAM modified P5 and P7 primers capable of targeting PAM-containing sequences. The sequences of standard universal primers P5 and P7 are shown in FIG. 1A (SEQ ID No. 1 and SEQ ID No. 2). The sequences of PAM-modified primers P5 and P7 are also shown in FIG. 1A (SEQ ID No. 3 and SEQ ID No. 4). Thus, in some embodiments, PAM-modified primers P5 and P7 are added to nucleic acid fragments in the library. In a specific embodiment, PAM-modified primers P5 and P7 are added to nucleic acid fragments using a limited-cycle PCR.

Figure 1C:
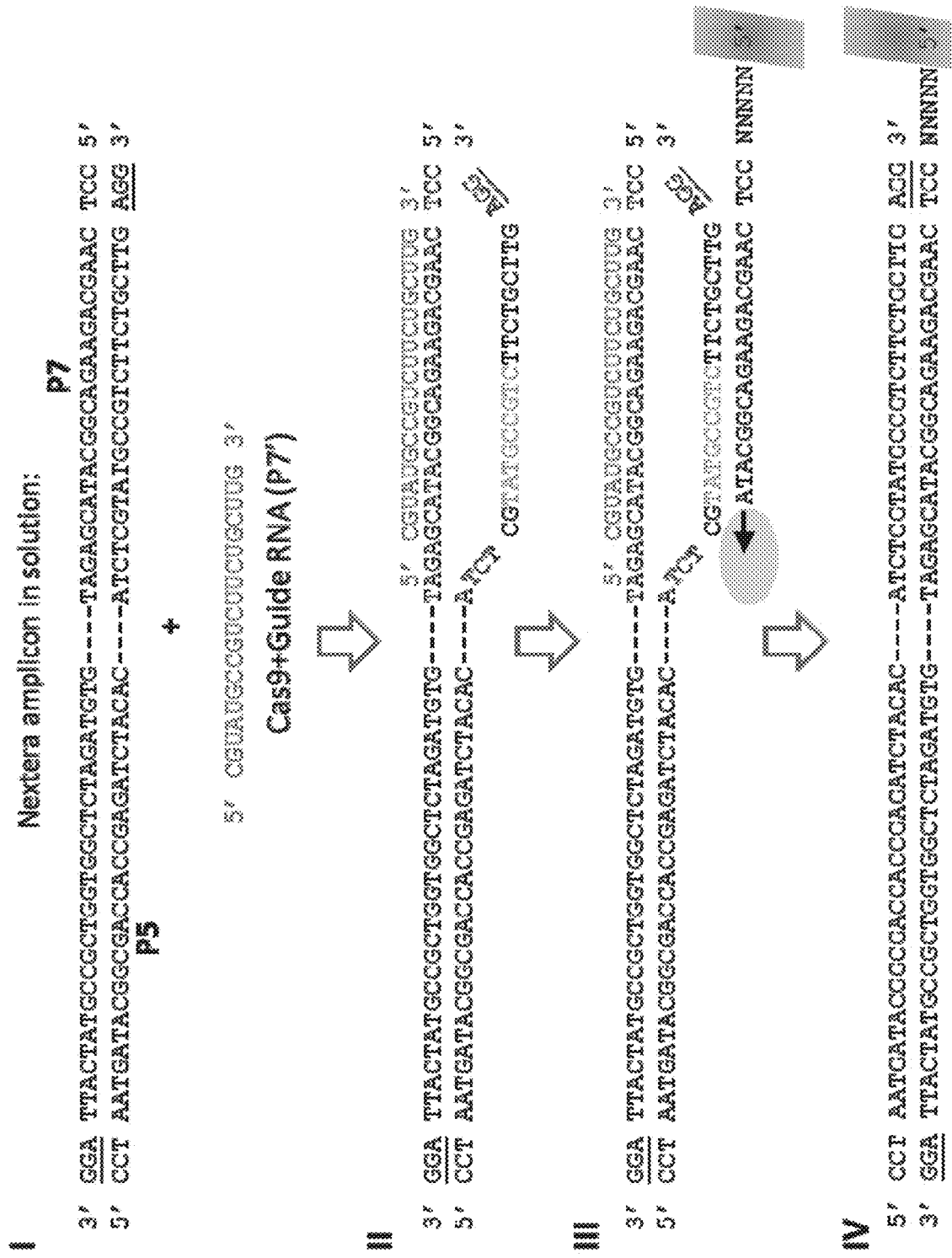
FIG. 1C illustrates one round of Cas9-mediated linear amplification using a crRNA targeting a modified P7 primer. 1C(I) depicts the DNA to be amplified which possesses appropriate primer sequences P5 and P7 (SEQ ID NO:09, and SEQ ID NO:10). The guide RNA targeting P7, bound to Cas9, is also shown as P7' (SEQ ID NO:08). 1C(II) shows the R loop created by Cas9 after the guide RNA has hybridized to the first strand. 1C(III) illustrates the immobilized P7 primer (SEQ ID NO:14, NNNNNTCCCAAGCAGAAGACGG-CATA) hybridizing to the displaced second strand, followed by polymerase extension. 1C(IV) shows the resulting extended primer P7 (SEQ ID NO: 15, TCCCAAGCAGAA-GACGGCATACAGAGAT; and SEQ ID NO:16, GTGTA-GATCTCGGTCGCCGTATCATTAGG). The resulting amplicon can be re-targeted by Cas9+crRNA as shown in step 1C(II). With both sides of the amplicon undergoing amplification (FIGS. 1B and 1C), exponential amplification can be achieved.

As shown in FIG. 1B-C, DNA fragments (e.g., Nextera amplicons in solution) contain P5 and P7 primer sequences (SEQ ID No. 1 and SEQ ID No. 2) at the ends of the amplicon. A CRISPR-Cas9 system containing a guide RNA of SEQ ID No. 7 targeting a region of P5 primer sequence (see FIG. 1B), and a CRISPR-Cas9 system containing a guide RNA of SEQ ID No. 8 targeting a region of P7 primer sequence (see FIG. 1C) are added. The CRISPR-Cas9 systems open some regions of double-stranded DNA to create R-loop structures near the two ends of the DNA fragment by binding crRNA to the primer sequences. Then truncated PAM-modified P5 and P7 primers (SEQ ID No. 5 and SEQ ID No. 6) can be used to amplify the DNA fragment.

Thus, in some embodiments, the first strand of the target double-stranded nucleic acid contains a universal sequence, and wherein the crRNA or the derivative thereof contains a sequence complementary to a region of the universal sequence. In some embodiments, the primer contains a sequence of a region of the universal sequence.

In some embodiments, the universal primer has a sequence of SEQ ID No. 3. In some embodiments, the crRNA contains a sequence of SEQ ID No. 7. In some embodiments, the primer contains a sequence of SEQ ID No. 5.

In some embodiments, the universal primer sequence has a sequence of SEQ ID No. 4. In some embodiments, the crRNA contains a sequence of SEQ ID No. 8. In some embodiments, the primer contains a sequence of SEQ ID No. 6.

In some embodiments, the first strand of the target double-stranded nucleic acid contains a first universal sequence, and wherein the crRNA or the derivative thereof of the first system contains a sequence complementary to a region of the first universal sequence, and the second strand of the target double-stranded nucleic acid contains a second universal sequence, and wherein the crRNA or the derivative thereof of the second system contains a sequence complementary to a region of the second universal sequence. In some embodiments, the first primer contains a sequence of a region of the first universal sequence, and the second primer contains a sequence of a region of the second universal sequence. In a specific embodiment, the first universal sequence has a sequence of SEQ ID No. 3, the crRNA or the derivative thereof of the first system contains a sequence of SEQ ID No. 7, and the first primer contains a sequence of SEQ ID NO. 5, and the second universal sequence has a sequence of SEQ ID No. 4, the crRNA or derivative thereof of the second system contains a sequence of SEQ ID No. 8, and the second primer contains a sequence of SEQ ID NO. 6.

The methods provided herein can be used in isothermal amplification for sequencing, e.g., in a cluster amplification developed by Illumina, Inc. (San Diego, Calif.). In some embodiments, the target nucleic acid of the present methods can be immobilized on a surface for amplification. For example, in some embodiments, immobilized nucleic acid fragments are amplified using cluster amplification methodologies as exemplified by the disclosures of U.S. Pat. Nos. 7,985,565 and 7,115,400, the contents of each of which is incorporated herein by reference in its entirety. The incorporated materials of U.S. Pat. Nos. 7,985,565 and 7,115,400 describe methods of solid-phase nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized nucleic acid fragments produced according to the methods provided herein. For example one or more clusters or colonies can be formed via solid-phase PCR whether one or both primers of each pair of amplification primers are immobilized.

As used herein, the terms "solid surface," "solid support" and other grammatical equivalents herein refer to any material that is appropriate for or can be modified to be appropriate for the attachment of a polynucleotide. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, solid supports and solid surfaces are located within a flow cell apparatus. In some embodiments, the solid support comprises a patterned surface suitable for immobilization of molecules in an ordered pattern. A "patterned surface" refers to an arrangement of different regions in or on an exposed layer of a solid support. In some embodiments, the solid support comprises an array of wells or depressions in a surface. The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. In some embodiments, the solid support or its surface is non-planar, such as the inner or outer surface of a tube or vessel. In some embodiments, the solid support comprises microspheres or beads. "Microspheres," "beads," "particles," or grammatical equivalents herein are intended to mean small discrete particles made of various material including, but are not limited to, plastics, ceramics, glass, and polystyrene. In certain embodiments, the microspheres are magnetic microspheres or beads. Alternatively or additionally, the beads may be porous. The bead sizes range from nanometers, e.g. 100 nm, to millimeters, e.g. 1 mm.

In other embodiments, the immobilized nucleic acid fragments are amplified in solution. For example, in some embodiments, the immobilized nucleic acid fragments are cleaved or otherwise liberated from the solid support and amplification primers are then hybridized in solution to the liberated molecules. In other embodiments, amplification primers are hybridized to the immobilized nucleic acid fragments for one or more initial amplification steps, followed by subsequent amplification steps in solution. Thus, in some embodiments an immobilized nucleic acid template can be used to produce solution-phase amplicons. It will be appreciated that any of the amplification methodologies described herein can be utilized with universal or target-specific primers to amplify immobilized nucleic acid fragments.

The nucleic acid amplified according to the method provided herein can be sequenced according to any suitable sequencing methodology, such as direct sequencing, including sequencing by synthesis, sequencing by ligation, sequencing by hybridization, nanopore sequencing and the like. In some embodiments, the immobilized DNA fragments are sequenced on a solid support. In some embodiments, the solid support for sequencing is the same solid support upon which the amplification occurs.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., 1996, *Analytical Biochemistry* 242 (1), 84-9; Ronaghi, 2001, *Genome Res.* 11(1), 3-11; Ronaghi et al., 1998, *Science* 281(5375), 363; U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al., 2003, *Science* 299, 682-686; Lundquist et al., 2008, *Opt. Lett.* 33, 1026-1028; Korlach et al., 2008, *Proc. Natl. Acad. Sci. USA* 105, 1176-1181, the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al., 2000, *Trends Biotechnol.*, 18, 147-151; Deamer et al., 2002, *Acc. Chem. Res.* 35:817-825; Li et al., 2003, Nat. Mater. 2:611-615), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al., 2007, *Clin. Chem.*, 53, 1996-200; Healy, 2007, Nanomed. 2, 459-481; Cockroft et al., 2008, *J. Am. Chem. Soc.*, 130, 818-820, the disclosures of which are incorporated herein by reference). In other nanopore sequencing embodiments, the DNA fragment to be sequenced creates a unique nanopore current signature using gamma phosphate modified nucleotides.

Methods for Enriching Polynucleotides

The present disclosure relates, in part, to utilizing CRISPR-Cas or Argonaute systems and derivatives thereof for target-specific enrichment.

Current target-specific enrichment protocols require that single-stranded nucleic acid be made prior to the target specific hybridization with probes. Among various advantages provided by the present disclosure, the present disclosure provides enrichment methods that can skip this step of generating single-stranded nucleic acid in the first place, and enable direct targeting to double-stranded nucleic acid, e.g., double-stranded DNA (dsDNA). Methods targeting directly to double-stranded DNA (either partly or completely double-stranded) have unique advantages over single-stranded enrichment strategies. For example, non-specific hybridization of single-stranded genomic DNA to targeted regions reduces specificity and often requires extensive stringency washing or other time-consuming steps; and single-stranded enrichment schemes often utilizes Cot-1 or other blocking DNA to reduce non-specific hybridization. These additives are not required from double-stranded DNA enrichment schemes, reducing both cost and number of required reagents. In addition, it is easier to make sequencing libraries from double-stranded DNA than from single-stranded DNA. As such, enrichment of double-stranded DNA allows library preparation (e.g., tagmentation) to occur after enrichment. For another example, since specificity (tree-like structures and non-specific hybridization is less of an issue with double-stranded DNA enrichment, potentially larger DNA fragments can be better specifically enriched compared to single-stranded DNA enrichment schemes. This is a particularly important advantage if one considers targeted sequencing in the context of haplotyping and assembly. Also, since longer DNA fragments can potentially be enriched, we have greater flexibility to where the target probe is designed. For example, we can avoid high polymorphic regions but still capture these regions. Also, fewer probes need to be used to capture large regions, reducing both capture probe cost and design.

In addition, the current protocols of target specific hybridization have slow kinetics and usually require high temperature. The present disclosure provides enzyme-driven sequence targeting methods that offer faster kinetics and easier workflow for enrichment. Because the hybridization to the target nucleic acid is enzyme driven in the present methods, the process can take place isothermally. In some embodiments, the method herein provides isothermal targeting of DNA at 20-37° C. Furthermore, the guide nucleic acid in the system herein provides for sequence specificity as well as flexible programming that enables multiplex targeted enrichment (e.g., targeting multiple targeted regions with more probes made in various ways including IVT from oligo pool). The present disclosure also provides methods for enriching and/or detecting polynucleotide variants with higher sensitivity and specificity. Furthermore, the present invention also provides methods for targeted sequencing using CRISPR-Cas or Argonaute systems.

In one aspect, the present disclosure provides a method for enriching a target nucleic acid using a nuclease system derived from a CRISPR-Cas or Argonaute system. The present disclosure is based, in part, on the capability of CRISPR-Cas or Argonaute system to specifically bind with a target nucleic acid. Such target specific binding by the CRISPR-Cas or Argonaute system provides methods for efficiently enriching target nucleic acid, e.g., by pulling down an element of CRISPR-Cas or Argonaute system that is associated with the target nucleic acid. CRISPR-Cas or Argonaute mediated nucleic acid enrichment bypasses traditionally required step of generating single-stranded nucleic acid prior to target specific binding, and enables directly targeting double-stranded nucleic acid, e.g., double-stranded DNA (dsDNA). In addition, CRISPR-Cas or Argonaute mediated nucleic acid binding is enzyme-driven, and thus it can offer faster kinetics and easier workflows for enrichment with lower temperature and/or isothermal reaction conditions.

In some embodiments, the present disclosure provides a method for enriching a target nucleic acid including: providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In other embodiments, provided herein is a method for enriching a target nucleic acid including: providing an endonuclease system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method provided herein further includes separating the target nucleic acid from the complex. In one embodiment, the CRISPR-Cas system or Argonaute system can be bound to a surface, e.g., in plate once it has found the targeted region. This can prevent dissociation of the complex pre-maturely, and thus improve efficiency of capture. In some embodiments, the method provided herein further includes amplifying the target nucleic acid sequence.

In some embodiments, the target nucleic acid provided herein is a double-stranded DNA (dsDNA).

In some embodiments, the endonuclease system provided herein is derived from a CRISPR-Cas system. In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally occurring CRISPR-Cas systems. CRISPR-Cas systems may include contain engineered and/or mutated Cas proteins. CRISPR-Cas systems may also contain engineered and/or programmed guide RNA.

The crRNA or the derivative thereof contains a target specific nucleotide region complementary or substantially complementary to a region of the target nucleic acid. In some embodiments, the crRNA or the derivative thereof contains a user-selectable RNA sequence that permits specific targeting of the enzyme to a complementary double-stranded DNA. In some embodiments, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the crRNA and the region of the target nucleic acid. In some embodiments, there are three base pair mismatches between the target specific nucleotide region of the crRNA and the region of the target nucleic acid. In some embodiments, there are four base pair mismatches between the target specific nucleotide region of the crRNA and the region of the target nucleic acid. In some embodiments, there are five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. A chimeric single-guided RNA (sgRNA) is described in Jinek et al., 2012, Science 337, 816-821, which is incorporated herein in its entirety. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. Isolated Cas9-crRNA complex from the *S. thermophilus* CRISPR-Cas system as well as complex assembled in vitro from separate components demonstrate that it binds to both synthetic oligodeoxynucleotide and plasmid DNA bearing a nucleotide sequence complementary to the crRNA. It has been shown that Cas9 has two nuclease domains—RuvC- and HNH-active sites/nuclease domains, and these two nuclease domains are responsible for the cleavage of opposite DNA strands. In some embodiments, the Cas9 protein is derived from Cas9 protein of *S. thermophilus* CRISPR-Cas system. In some embodiments, the Cas9 protein is a multi-domain protein having about 1,409 amino acids residues.

In some embodiments, the Cas9 protein or the variant thereof retains the two nuclease domains and is able to cleave opposite DNA strands and produce a double-stranded DNA break. The present method is partially based on a surprising discovery that wild-type Cas9 protein that retains the two nuclease domains can remain at the binding site following DNA cleavage with sufficient strength and length, so that to enable pulling down the DNA-endonuclease system complex through the endonuclease system. As illustrated in FIG. 2A-2B, the CRISPR-Cas system containing a wild type Cas9 protein is added to a solution containing a target Braf sequence. The system is labeled with biotinylated dUTP, and streptavidin beads are added to pull down the system with its associated DNA fragments. As shown in the right panel of FIG. 2A-2B, the cleaved DNA fragments are detected from the bead elution, indicating the association between the enzyme system and the DNA after the cleavage.

In other embodiments, the Cas9 protein or the variant thereof is a Cas9 nickase and is able to produce a single-stranded nucleic acid nick, e.g., a single-stranded DNA nick. A nickase variant of Cas9 protein stays with the target nucleic acid after creating a nick, and thus it can be used for target specific enrichment. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A.

In other embodiments, the systems provided herein are derived from Argonaute systems. In some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

In some embodiments, the 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucelotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the present method can be used to enrich a target nucleic acid fragment in a library of nucleic acid fragments, e.g., prepared using Illumina's Nextera library preparation.

In some embodiments, the Cas9 protein or the variant thereof or Argonaute protein or the variant thereof is a nuclease-null variant of the Cas9 or Argonaute protein. For example, in some embodiments, both RuvC- and HNH-active sites/nuclease domains of a Cas9 protein are mutated. A nuclease-null variant of the Cas9 protein or Argonaute protein binds to double-stranded DNA, but not cleave the DNA, and thus it can be used for target specific DNA enrichment too.

A target nucleic acid can be separated by pulling down its associated CRISPR-Cas or Argonaute system or elements thereof. In some embodiments, the endonuclease system is labeled, and the enzyme-nucleic acid complex is pulled down through the label. In some embodiments, the guide nucleic acid is labeled. In one embodiment, the guide nucleic acid, e.g., crRNA or 5' phosphorylated single-stranded nucleic acid, is labeled with biotin. In other embodiments, the Cas protein or the Argonaute, or the variant thereof, is labeled with a capture tag. The protein capture tag includes, but not limited to, GST, Myc, hemagglutinin (HA), Green fluorescent protein (GFP), flag, His tag, TAP tag, and Fc tag. Other protein capture tags, e.g., affinity tags, recognized in the art can also be used in the present methods. Those skilled in the art will recognize that a protocol chosen for the purification step will be specific to the tag used. In some embodiments, antibodies or fragments thereof, e.g., anti-Cas9 antibodies or anti-Argonaute antibodies, can also be used to separate the complex.

In another aspect, binding of a guide nucleic acid to a region of a target double-stranded nucleic acid disrupts the interaction between the two strands of the target nucleic acid, and thereby creates a loop structure exposing the strand non-complementary to the guide nucleic acid. This exposed strand can be subjected to hybridization with another nucleotide probe as provided herein. One advantage provided by the method herein is double specificity for the enrichment—one from the guide nucleic acid and the other from the probe.

In one embodiment, the present disclosure provides a method for enriching a target double-stranded nucleic acid including providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; contacting the target double-stranded nucleic acid with the endonuclease system to form a first complex; hybridizing a labeled nucleic acid to a second strand of the target double-stranded nucleic acid to form a second complex, the second strand of the target double-stranded nucleic acid being non-complementary to the crRNA or the derivative thereof, and separating the second complex and thereby enriching for the target nucleic acid.

In another embodiment, the present disclosure provides a method for enriching a target double-stranded nucleic acid including providing an endonuclease system having: a 5' phosphorylated single-stranded nucleic acid or a derivative thereof, and an Argonaute protein or a variant thereof or a variant thereof, wherein the 5' phosphorylated single-stranded nucleic acid or the derivative thereof contains a target-specific nucleotide region complementary to a region of a first strand of the target double-stranded nucleic acid; contacting the target double-stranded nucleic acid with the endonuclease system to form a first complex; hybridizing a labeled nucleic acid to a second strand of the target double-stranded nucleic acid to form a second complex, the second strand of the target double-stranded nucleic acid being non-complementary to the 5' phosphorylated single-stranded nucleic acid or the derivative thereof, and separating the second complex and thereby enriching for the target nucleic acid.

In some embodiments, the method of the present disclosure further includes separating the target double-stranded DNA sequence from the second complex. In some embodiments, the method the present application further includes amplifying the targeted double-stranded DNA sequence.

In some embodiments, the target nucleic acid provided herein is a double-stranded DNA (dsDNA).

In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In other embodiments, the systems provided herein are derived from Argonaute systems. In some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

In some embodiments, the 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucelotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In another aspect, the target nucleic acid can be fragmented and linked to an adaptor, preparing for other procedures such as sequencing. In some embodiments, the target nucleic acid is further subjected to a transposase mediated tagmentation that results in fragmentation of the target nucleic acid and ligation of adaptors to the 5' end of both strands of double-stranded DNA fragments. Optionally, the target nucleic acid can be fragmented and adaptors can be added to the 5' and 3' ends using tagmentation or transposition as described in U.S. Publication No. 2010/0120098, which is incorporated by reference herein in its entirety. Briefly, a transposition reaction is a reaction wherein one or more transposons are inserted into target nucleic acids at random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. Exemplary transposition complexes, suitable for use in the methods provided herein, include, but are not limited to, those formed by a hyperactive Tn5 transposase and a Tn5-type transposon end or by a MuA transposase and a Mu transposon end comprising R1 and R2 end sequences (see, e.g., Goryshin and Reznikoff, *J. Biol. Chem.* 273: 7367, 1998; and Mizuuchi, *Cell* 35: 785, 1983; Savilahti et al., *EMBO J.* 14: 4893, 1995; which are incorporated by reference herein in their entireties). However, any transposition system that is capable of inserting a transposon end with sufficient efficiency to tag target nucleic acids for its intended purpose can be used in the provided methods. Other examples of known transposition systems that could be used in the provided methods include, but are not limited to, *Staphylococcus aureus* Tn552, Ty1, Transposon Tn7, Tn/O and IS10, Mariner transposase, Tel, P Element, Tn3, bacterial insertion sequences, retroviruses, and retrotransposon of yeast (see, e.g., Colegio et al., 2001, *J. Bacteriol.* 183: 2384-8; kirby et al., 2002, *Mol. Microbiol.* 43: 173-86; Devine and Boeke, 1994, *Nucleic Acids Res.,* 22: 3765-72; International Patent Application No. WO 95/23875; Craig, 1996, *Science* 271: 1512; Craig, 1996, Review in: *Curr Top Microbiol Immunol.* 204: 27-48; Kleckner et al., 1996, *Curr Top Microbiol Immunol.* 204: 49-82; Lampe et al., 1996, *EMBO J.* 15: 5470-9; Plasterk, 1996, *Curr Top Microbiol Immunol* 204: 125-43; Gloor, 2004, *Methods Mol. Biol.* 260: 97-114; Ichikawa and Ohtsubo, 1990, *J Biol. Chem.* 265: 18829-32; Ohtsubo and Sekine, 1996, *Curr. Top. Microbiol. Immunol.* 204: 1-26; Brown et al., 1989, *Proc Natl Acad Sci USA* 86: 2525-9; Boeke and Corces, 1989, *Annu Rev Microbiol.* 43: 403-34; which are incorporated herein by reference in their entireties). In some embodiments, the method of the present disclosure further comprises removing the transposase enzyme and adding to the ends of the adapted DNA fragments by PCR.

In some embodiments, the tagmentation is performed after the target nucleic acid is enriched.

In some embodiments, the guide nucleic acid, e.g., the RNA in the CRISPR-Cas system (e.g., a crRNA or a derivative thereof, a sgRNA, and a tracrRNA or a derivative thereof), or the 5' phosphorylated single-stranded nucleic acid (e.g., a gDNA), contains a transposon end, and the method of the present disclosure further includes adding a transposase. The added transposase can assemble on the transposon end and the target DNA is thereby cleaved by the transposase. In some embodiments, the transposon end is a mosaic end (ME), and the transposase is a Tn5 transposase.

In some embodiments, the nuclease system provided herein further includes a transposase, and thus transposase is part of the endonuclease system, and the method of the present disclosure further includes adding transposon end to the target DNA sequence; and tagmenting the target DNA sequence by the transposase. In some embodiments, the transposase binds to a nucleotide sequence of the endonuclease system. In some embodiments, the transposase binds to a crRNA or a derivative thereof. In some embodiments, the transposase binds to a tracrRNA or a derivative thereof. In some embodiments, the transposase binds to a sgRNA or a chimeric polynucleotide having a crRNA polynucleotide and a tracrRNA polynucleotide. In some embodiments, the transposase binds to a 5' phosphorylated single-stranded nucleic acid or a derivative thereof. In some embodiments, the transposon end is a mosaic end (ME), and the transposase is a Tn5 transposase.

In another aspect, the present disclosure provides methods for enriching and/or detecting target nucleic acid in a population of cell free DNA using CRISPR-Cas or Argonaute systems. Cell free DNA in plasma or serum holds enormous potential as a non-invasive diagnostic tool in many areas of medicine. For example, cell free fetal DNA has been studied and even optimized for testing non-compatible RhD factors, sex determination for X-linked genetic disorders, testing for single gene disorders, identification of preeclampsia, and so on. For instance, sequencing the fetal cell fraction of cell free DNA in maternal plasma is a reliable approach for detecting copy number changes associated with fetal chromosome anueploidy. For another instance, sequencing cell free DNA isolated from cancer patients (also called circulating tumor DNA) has been used to detect mutations in key genes that have relevance for treatment decisions. The present disclosure provides methods for improving enriching and/or detecting target DNA sequences in cell free DNA.

In some embodiments, the present disclosure provides a method for enriching a target nucleic acid including obtaining a population of cell free DNA (cfDNA) from a subject's plasma or serum, the population of cell free DNA containing the target nucleic acid; providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In other embodiments, the present disclosure provides a method for enriching a target nucleic acid including obtaining a population of cell free DNA (cfDNA) from a subject's plasma or serum, the population of cell free DNA containing the target nucleic acid; providing an endonuclease system having: a 5' phosphorylated single-stranded nucleic acid or a derivative thereof, and an Argonaute protein or a variant thereof, wherein the 5' phosphorylated single-stranded nucleic acid or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method provided herein further includes separating the target DNA sequence from the complex. In some embodiments, the method provided herein further includes amplifying the targeted DNA sequence. In some embodiments, the target nucleic acid provided herein is a double-stranded DNA (dsDNA).

In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In other embodiments, the systems provided herein are derived from Argonaute systems. In some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

In some embodiments, the 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucelotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the target DNA is in a fetal cell faction of the cell free DNA, and the cell free DNA is from maternal plasma. Protocols for extracting cell free fetal DNA are known in the art (see. e.g., Li et al., 2004, *Clinical Chemistry* 50 (6): 1002-1011; and Li et al., 2005, *The Journal of the American Medical Association* 293 (7): 843-849, which are incorporated herein by reference in their entireties). Many protocols for extracting the fetal DNA from the maternal plasma use the size of the fetal DNA to distinguish it from the maternal DNA. Typical steps for isolation of plasma from maternal blood include centrifugation, followed by isolation and purification of cell-free DNA (see, e.g., Chiu et al., 2001, *Clinical Chemistry* 47 (9): 1607-1613). Optionally, protocol developed by Legler et al. can be used for extracting cell free fetal DNA (see Legler et al. 2007, *Prenatal Diagnosis* 27 (9): 824-829). Optionally, formaldehyde can be added to maternal blood samples to increase the percentage of cell free fetal DNA. It has been shown that formaldehyde can stabilize intact cells, and inhibit further release of maternal DNA (see, e.g., Dhallan et al. 2004, *The Journal of the American Medical Association* 291 (9): 1114-1119).

In some embodiments, the subject is a cancer patient. A tumor itself is usually the major source of tumor DNA. However, acquiring DNA through a biopsy is invasive and risky if possible at all. Cell-free circulating tumor DNA in the bloodstream released from dying tumor cells provides another useful tool for detecting somatic mutation present in the tumors. Cell free circulating tumor DNA with mutations has been identified in many types of cancers at both early stage and advanced stage. In addition, the amount of cell free circulating DNA has been shown to increase as the cancer advances. Accordingly, cell free circulating DNA can also be used as a way of monitoring tumor progression and testing whether a patient's tumor would respond to targeted drug treatments (see, e.g., Bettegowda et al., 2014, *Sci. Transl. Med*, 6(224): 24). The present disclosure provides a method for enriching and/or detecting a target DNA sequence in the cell free circulating DNA from a cancer patient. In one embodiment, the cancer patient has pancreatic, ovarian, colorectal, bladder, gastroesophageal, breast, melanoma, hepatocellular, or head and neck cancer. In some embodiments, the cancer patient has brain, renal, prostate, or thyroid cancer. In some embodiments, the cancer patient has carcinoma. In some embodiments, the cancer patient has sarcoma. In some embodiments, the cancer patient has a lymphoma or leukemia. In some embodiments, the method provided herein is used to diagnose a cancer. In some embodiments, the method provided herein is used to monitor tumor progression and/or test a tumor patient's response to targeted drug treatments.

In some embodiments, the target nucleic acid contains a single nucleotide variant (SNV). In some embodiments, the SNV contains a single nucleotide polymorphism (SNP). In some embodiments, the SNV contains a point mutation. Single nucleotide polymorphism (SNP) is a common type of genetic variation which includes polymorphism in a DNA position at which two or more alternative bases occur at appreciable frequency in the people population (usually more than or equal to 1%). Point mutations are base variations with the frequency less than 1%. Single nucleotide polymorphism (SNP) and point mutations represent the largest source of diversity in the genome of a human. These single nucleotide polymorphisms (SNP) and point mutations can serve as biological markers for locating a disease on the human genome map because they are usually located near a gene associated with a certain disease. Thus, detection of single nucleotide polymorphisms (SNPs), point mutations, and similar mutations are of great importance to clinical activities, human health, and control of genetic disease. Detection of fetal or cancer related SNV by sequencing cell free DNA can be difficult since these variants often are present at a very low percentage of total cell free DNA (typically 0.1% and below). One advantage provided by the present disclosure is a more sensitive method for detecting and/or enriching a DNA sequence having SNV. In one embodiment, the method of the present disclosure allows detection of SNV present in a cell free DNA sample in the 0.1% to 0.01% frequency range. In one embodiment, the method provided herein enriches and/or detects SNV present in a cell free DNA sample in the 0.01% to 0.05% frequency range. In some embodiments, the method provided herein enriches and/or detects SNV present in a cell free DNA sample at about 0.01%, 0.02%, 0.03%, 0.04%, 0.05%, 0.06%, 0.07%, 0.08%, 0.09%, or 0.1% frequency.

As an alternative to direct enrichment of the target nucleic acid sequence containing SNV, the present disclosure also provides a method for enriching nucleic acid sequence containing SNV by destroying other genotypes or polynucleotides that do not contain SNV using CRISPR-Cas or Argonaute systems.

In some embodiments, the present disclosure provides a method for detecting single nucleotide variant (SNV) including obtaining a population of cell free DNA from a subject's plasma or serum; providing a first endonuclease system having a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a region of a first target nucleic acid, and wherein the first Cas protein has nuclease activity; cleaving the first target nucleic acid using the endonuclease system, and amplifying a second target nucleic acid using Polymerase Chain Reaction (PCR), wherein the second target nucleic acid contains a single nucleotide variant version of the first target nucleic acid.

In other embodiments, the present disclosure provides a method for detecting single nucleotide variant (SNV) including: obtaining a population of cell free DNA from a subject's plasma or serum; providing a first endonuclease system having: a first 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a region of a first target nucleic acid, and wherein the first Argonaute protein has nuclease activity; cleaving the first target nucleic acid using the first endonuclease system, and amplifying a second target nucleic acid using Polymerase Chain Reaction (PCR), wherein the second target nucleic acid contains a single nucleotide variant version of the first target nucleic acid.

In some embodiments, the second target nucleic acid provided herein is a double-stranded DNA (dsDNA).

In some embodiments, the first endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the first crRNA or the derivative thereof contains a user-selectable RNA sequence that permits specific targeting of the enzyme to a complementary double-stranded nucleic acid. In some embodiment, the user-selectable RNA sequence contains 20-50 nucleotides complementary to a region of the first target DNA sequence. In some embodiments, the first target specific nucleotide region of the crRNA has 100% base pair matching with the region of first the target nucleic acid. In some embodiments, there is one base pair mismatch between the first target specific nucleotide region of the crRNA and the region of the first target nucleic acid. In some embodiments, there are two, three, four, or five base pair mismatches between the first target specific nucleotide region of the crRNA and the region of the first target nucleic acid.

In some embodiments, the first endonuclease system provided herein further includes a trans-activating crRNA (tracrRNA) or a derivative thereof. In some embodiments, the first crRNA or the derivative thereof provided herein is a polynucleotide having a crRNA polynucleotide fused to a tracrRNA polynucleotide. In one embodiment, the first Cas protein or the variant thereof provided herein can be directed by a chimeric sgRNA to any genomic locus followed by a 5'-NGG protospacer-adjacent motif (PAM).

In some embodiments, the first Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues. In some embodiments, the Cas9 protein or the variant thereof retains the two nuclease domains and is able to cleave opposite DNA strands and produce a double-stranded DNA break.

In other embodiments, the systems provided herein are derived from Argonaute systems. In some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

In some embodiments, the 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucleotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the second target nucleic acid contains a single nucleotide variant (SNV). In some embodiments, the SNV contains a single nucleotide polymorphism (SNP). In some embodiments, the SNV contains a point mutation. In one embodiment, the method of the present disclosure allows detection of SNV present in a cell free DNA sample in the 0.1% to 0.01% frequency range. In one embodiment, the method provided herein enriches and/or detects SNV present in a cell free DNA sample in the 0.01% to 0.05% frequency range. In some embodiments, the method provided herein enriches and/or detects SNV present in a cell free DNA sample at about 0.01%, 0.02%, 0.03%, 0.04%, 0.05%, 0.06%, 0.07%, 0.08%, 0.09%, or 0.1% frequency.

Alternatively, two endonuclease systems can be provided: the first endonuclease system is used to digest the nucleic acid that does not contain SNV, and the second endonuclease system is used to pull down the nucleic acid with SNV.

In some embodiments, the method herein further includes providing a second endonuclease system having a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a second target-specific nucleotide region complementary to a region of the second target nucleic acid; contacting the second target nucleic acid with the second endonuclease system to form a complex, and separating the complex and thereby enriching for the second target nucleic acid.

In some embodiments, the method herein further includes providing a second endonuclease system having a second 5' phosphorylated single-stranded nucleic acid or a derivative thereof, and a second Argonaute protein or a variant thereof, wherein the second 5' phosphorylated single-stranded nucleic acid or the derivative thereof contains a second target-specific nucleotide region complementary to a region of the second target nucleic acid; contacting the second target nucleic acid with the second endonuclease system to form a complex, and separating the complex and thereby enriching for the second target nucleic acid.

In some embodiments, the method provided herein further includes separating the second target nucleic acid from the complex. In some embodiments, the second target nucleic acid provided herein is a double-stranded DNA (dsDNA).

In some embodiments, the second endonuclease system provided herein is a Type I CRISPR-Cas system or a derivative thereof. In some embodiments, the second endonuclease system provided herein is a Type II CRISPR-Cas system. In some embodiments, the second endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the second crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the second endonuclease system provided herein further includes a trans-activating crRNA (tracrRNA) or a derivative thereof. In some embodiments, the crRNA or the derivative thereof provided herein is a polynucleotide comprising a crRNA polynucleotide fused to a tracrRNA polynucleotide.

In some embodiments, the second Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of a Cas9 protein, in which both RuvC- and HNH-active sites/nuclease domains are mutated. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In other embodiments, the systems provided herein are derived from Argonaute systems. In some embodiments, the system is an Ago subfamily system or a derivative thereof. In other embodiments, the system is a Piwi subfamily system or a derivative thereof. In some specific embodiments, the Argonaute protein is *Natronobacterium gregorgi* Argonaute (Ng Argonaute) or a variant thereof.

In some embodiments, the 5' phosphorylated single-stranded nucleic acid or the derivative thereof contains a target specific nucleotide region complementary or substantially complementary to a region of the target nucleic acid. In some embodiments, the 5' phosphorylated single-stranded nucleic acid or the derivative thereof contains a user-selectable DNA sequence that permits specific targeting of the enzyme to a complementary double-stranded DNA. In some embodiments, the user-selectable DNA sequence contains 20-50 nucleotides complementary or substantially complementary to a region of the target DNA sequence. In some embodiments, the 5' phosphorylated single-stranded nucleic acid is user-selectable single-stranded DNA sequence of less than 100 nucleotides. In some embodiments, the 5' phosphorylated single-stranded nucleic acid is a single-stranded DNA of less than 50 nucleotides. In some embodiments, the 5' phosphorylated single-stranded nucleic acid is a single-stranded DNA of less than 25 nucleotides. Example lengths of the single-stranded DNA include 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 nucleotides. In some embodiments, the user-selectable DNA sequence contains less than 20 nucleotides complementary or substantially complementary to a region of the target DNA sequence. Exemplary user-selectable DNA sequence contains 1, 2, 3, 4, 5, 6, 7, 8, 9, 10, 11, 12, 13, 14, 15, 16, 17, 18, or 19 nucelotides complementary or substantially complementary to a region of the target DNA sequence.

In some embodiments, the target specific nucleotide region of the 5' phosphorylated single-stranded nucleic acid has 100% base pair matching with the region of the target nucleic acid. In some embodiments, the target specific nucleotide region of the 5' phosphorylated single-stranded nucleic acid has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the 5' phosphorylated single-stranded nucleic acid and the region of the target nucleic acid. In some embodiments, there are three base pair mismatches between the target specific nucleotide region of the 5' phosphorylated single-stranded nucleic acid and the region of the target nucleic acid. In some embodiments, there are four base pair mismatches between the target specific nucleotide region of the 5' phosphorylated single-stranded nucleic acid and the region of the target nucleic acid. In some embodiments, there are five base pair mismatches between the target specific nucleotide region of the 5' phosphorylated single-stranded nucleic acid and the region of the target nucleic acid.

The Argonaute systems provided herein include engineered and/or programmed nuclease systems derived from naturally occurring Argonaute systems. Argonaute systems may include contain engineered and/or mutated Argonaute proteins. Argonaute systems may also contain engineered and/or programmed guide nucleic acid. In some embodiments, the Argonaute protein or a variant thereof is engineered to remove the endonuclease activity so that the Argonaute system does not generate double-stranded or single-stranded DNA breaks. In other embodiments, the Argonaute protein or a variant thereof is engineered to be able to generate single-stranded DNA breaks.

In some embodiments, the second target nucleic acid is in a fetal cell faction of the cell free DNA, and the cell free DNA is from maternal plasma. In some embodiments, the subject is a cancer patient. In one embodiment, the cancer patient has pancreatic, ovarian, colorectal, bladder, gastroesophageal, breast, melanoma, hepatocellular, or head and neck cancer. In some embodiments, the cancer patient has brain, renal, prostate, or thyroid cancer. In some embodiments, the cancer patient has carcinoma. In some embodiments, the cancer patient has sarcoma. In some embodiments, the cancer patient has a lymphoma or leukemia. In some embodiments, the method provided herein is used to diagnose a cancer. In some embodiments, the method provided herein is used to monitor tumor progression and/or test a tumor patient's response to targeted drug treatments.

In yet another aspect, the present disclosure provides a method for labeling a target nucleic acid sequence using CRISPR-Cas or Argonaute system containing a nickase. The nickase provided herein can introduce target specific nicks to the double-stranded nucleic acid. The nicks can be further used to insert capture tags, such as biotinylated dNTP, oligo probes, or double-stranded nucleic acid adapters, for enrichment strategies of the target nucleic acid. The current methods of a single-stranded nucleic acid enrichment schemes requires generating a "tree structure" of hybridized products, and such structure usually reduces specificity. The method provided herein directly targets to double-stranded nucleic acid and thus circumvents the need of creating such a "tree structure." In addition, the method provided here enables enrichment of long nucleic acid fragments.

In some embodiments, the method provided herein includes generating one single-stranded nick, and from this nick a nick translation is performed to introduce a capture label for recovering the target nucleic acid. In other embodiments, the method provided herein includes generating two consecutive single-stranded nicks on the same strand of the target nucleic acid. The single-stranded nucleic acid product between the two nicks can be replaced with a capture label for recovering the target nucleic acid. In yet other embodiments, the method provided herein includes generating two consecutive single-stranded nicks on the opposite strands of the target nucleic acid, and thus generate a double-stranded nucleic acid break that can be linked to an adapter for enrichment.

In some embodiment, the present disclosure provides a method for labeling a target nucleic acid including providing a first nuclease system having a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a first region of the target nucleic acid, and wherein the first Cas protein contains one inactivated nuclease domain; contacting a double-stranded nucleic acid containing the target nucleic acid with the first nuclease system to generate a first single-stranded nick at the first region of the target nucleic acid, and labeling the target nucleic acid.

In other embodiments, the present disclosure provides a method for labeling a target nucleic including providing a first nuclease system having a first 5' phosphorylated single-stranded nucleic acid or a derivative thereof, and a first Argonaute protein or a variant thereof, wherein the first 5' phosphorylated single-stranded nucleic acid or the derivative thereof contains a first target-specific nucleotide region complementary to a first region of the target nucleic acid, and wherein the first Argonaute protein is capable of generating a single-stranded nick; contacting a double-stranded nucleic acid containing the target nucleic acid with the first nuclease system to generate a first single-stranded nick at the first region of the target nucleic acid, and labeling the target nucleic acid.

In some embodiments, the method herein further includes separating the target nucleic acid through the labeling and thereby enriching the target nucleic acid. In some embodiments, the method provided herein further includes amplifying the target nucleic acid.

In some embodiments, the first nuclease system provided herein further includes a trans-activating crRNA (tracrRNA). In some embodiments, the first crRNA or the derivative thereof provided herein is a polynucleotide having a crRNA polynucleotide fused to a tracrRNA polynucleotide. In some embodiments, the first nuclease system provided herein is a Type II CRISPR-Cas system or a derivative thereof. In some embodiments, the first Cas protein or the variant thereof is a Cas9 protein or a variant thereof. In some embodiments, the Cas9 protein or the variant thereof contains one inactivated nuclease domain with a mutation in the domain that cleaves a target nucleic acid strand that is complementary to the first crRNA. In some embodiments, the mutation is D10A. In some embodiments, the first Cas9 protein or the variant thereof contains one inactivated nuclease domain with a mutation in the domain that cleaves a target nucleic acid strand that is non-complementary to the first crRNA. In some embodiments, the mutation is H840A.

In some embodiments, the method of the present disclosure further includes performing a nick translation. In some embodiments, the nick translation provided herein is performed by using a nick translation polymerase selected from a group consisting of DNA Pol 1, Bst, and Taq. Other nick translation polymerases known in the art are also included in the method provided herein. In some embodiments, the nick translation provided herein is performed in a reaction mixture containing biotinylated dNTPs. In some embodiments, the biotinylated dNTPs provided herein are biotinylated dUTPs. In some embodiments, the method of the present disclosure further includes adding magnetic streptavidin beads to enrich biotinylated target DNA.

In some embodiments, the method of present disclosure further includes providing a second nuclease system having a second crRNA or a derivative thereof, and a second Cas protein or a variant thereof, wherein the second crRNA or the derivative thereof contains a second target-specific nucleotide region complementary to a second region of the target nucleic acid, and wherein the second Cas protein contains one inactivated nuclease domain, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid.

In some embodiments, the method of present disclosure further includes providing a second nuclease system having: a second 5' phosphorylated single-stranded nucleic acid or a derivative thereof, and a second Argonaute protein or a variant thereof, wherein the second 5' phosphorylated single-stranded nucleic acid or the derivative thereof contains a second target-specific nucleotide region complementary to a second region of the target nucleic acid, and wherein the second Argonaute protein is capable of generating a single-stranded nick, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid.

In some embodiments, the first single-stranded nick and the second single-stranded nick are on the same strand of the target nucleic acid.

For example, in some embodiments, the first region of the target nucleic acid and the second region of the target nucleic acid are on the same strand of the target nucleic acid, and the first Cas9 protein and the second Cas9 protein both contain a mutation in the domain that cleaves a target nucleic acid strand that is complementary to their respective crRNAs, so that the first single-stranded nick and the second single-stranded nick are on the same strand of the target nucleic acid. In some embodiments, the first Cas protein is a first Cas9 protein containing one inactivated nuclease domain having a first mutation in the domain that cleaves a target nucleic acid strand that is complementary to the first crRNA, and the second Cas protein is a second Cas9 protein containing one inactivated nuclease domain containing a second mutation in the domain that cleaves a target nucleic acid strand that is complementary to the second crRNA. In some embodiments, the first mutation and the second mutation are both D10A.

In some embodiments, the first region of the target nucleic acid and the second region of the target nucleic acid are on the same strand of the target nucleic acid, and the first Cas9 protein and the second Cas9 protein both contain a mutation in the domain that cleaves a target nucleic acid strand that is non-complementary to their respective crRNAs, so that the first single-stranded nick and the second single-stranded nick are on the same strand of the target nucleic acid. In some embodiments, the first Cas protein is a first Cas9 protein containing one inactivated nuclease domain having a first mutation in the domain that cleaves a target nucleic acid strand that is non-complementary to the first crRNA, and the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, the first region of the target nucleic acid and the second region of the target nucleic acid are on different strands of the target nucleic acid, and the two Cas9 proteins retain different nuclease domains, so that the first single-stranded nick and the second single-stranded nick are on the same strand of the target nucleic acid. In some embodiments, the first Cas protein is a first Cas9 protein containing one inactivated nuclease domain with a first mutation in the domain that cleaves a target nucleic acid strand that is complementary to the first crRNA, and the second Cas protein is a second Cas9 protein containing one inactivated nuclease domain with a second mutation in the domain that cleaves a target nucleic acid strand that is non-complementary to the second crRNA. In some embodiments, the first mutation is D10A, and said second mutation is H840A.

In some embodiments, the space between the first single-stranded nick and the second single-stranded nick is from 20 base pairs (bp) to 10 kp. In some embodiments, the space between the first single-stranded nick and the second single-stranded nick is from 20 base pairs (bp) to 5 kp. In some embodiments, the space between the first single-stranded nick and the second single-stranded nick is from 20 base pairs (bp) to 1000 bp. In some embodiments, the space between the first single-stranded nick and the second single-stranded nick is from 20 base pairs (bp) to 500 bp. In some embodiments, the space between the first single-stranded nick and the second single-stranded nick is about 20 bp, 30 bp, 40 bp, 50 bp, 60 bp, 70 bp, 80 bp, 90 bp, 100 bp, 200 bp, 300 bp, 400 bp, or 500 bp.

In some embodiments, the method of the present disclosure further includes adding a capture probe; and exchanging a single-stranded nucleic acid product between the first single-stranded nick and the second single-stranded nick with the capture probe, wherein the capture probe is able to hybridize to a nucleic acid strand complementary to the single-stranded nucleic acid product. In some embodiments, the sequence of the capture probe is 10% to 100% identical to the sequence of the single-stranded nucleic acid product. In some embodiments, the sequence of the capture probe is about 10%, 20%, 30%, 40%, 50%, 60%, 70%, 80%, or 90% identical to the sequence of the single-stranded nucleic acid product. In some embodiments, the capture probe provided herein is a biotinylated probe. In some embodiments, the method of the present disclosure further includes adding magnetic streptavidin beads to enrich the target nucleic acid.

In some embodiments, the nickases in the nuclease systems provide herein generate two consecutive single-stranded nicks on the same strand of the target DNA. Two enzymes systems are added with each targeting to a different region of the target DNA sequence, and thus two consecutive single-stranded nicks are generated on the same strand. The single-stranded DNA product between the two nicks is then replaced with a capture probe, e.g., a biotinylated capture probe, for an enrichment step.

In some embodiments, the capture probe contains an overhang nucleotide sequence, the overhang nucleotide sequence is substantially complementary to an oligo immobilized on a surface. Therefore, the overhang can be used to pull down the target DNA by annealing the overhang to a complementary oligo immobilized on a surface. In one embodiment, the overhang contains or is complementary to the universal Illumina® capture primers P5 (available from Illumina, Inc, San Diego, Calif.). The surface can be an external part or external layer of a solid support. The solid support can be a rigid solid and optionally can be impermeable to liquids or gases. The solid support can also be a semi-rigid solid, for example, being permeable to liquids or gases. The surface can be in contact with another material such as a gas, liquid, gel, second surface of a similar or different solid support, metal, or coat. The surface, or regions thereof, can be substantially flat. The surface can have surface features such as wells, pits, channels, ridges, raised regions, pegs, posts or the like. In some embodiments, a surface or region thereof can be located in a vessel such as a well, tube, channel, cuvette, Petri plate, bottle or the like. A useful vessel is a flow-cell. Exemplary flow-cells are those that are commercially available from Illumina, Inc (San Diego, Calif.). Another useful vessel is a well in a multiwell plate or microtiter plate. In some embodiments, the method provided herein further includes Nextera library preparation and clustering on the surface. In some embodiments, transposition can be performed prior to flow cell capture. Various embodiments have been described in context of a commercially available solid phase platform, e.g., available from Illumina Inc. (San Diego, Calif.), and those skilled in the art will understand that any of the various embodiments can be performed with various other solid phase configurations well known in the art. Such configurations essentially include solid phase and capture probe.

In other embodiments, the methods provided herein can be used to introduce specific gaps in repeat regions. In one embodiment, the capture probe has a "hairpin" or is a mismatched probe with 5' and 3' regions complementary to the target DNA. As a result, each repeat unit is replaced with a unique marker (or barcode) allowing the introduction of landmarks. The landmarks can be used for assembly of repeat regions or counting the exact number of repeats.

Certain polymerases e.g., Phi29, can initiate a nick translation from a gap. Thus, in yet other embodiments, the space between the first single-stranded nick and the second single-stranded nick on the same strand of the target nucleic acid is 1 bp to 20 bp. In some embodiments, the method provided herein can further comprise performing a nick translation. In some embodiments, the nick translation is performed by using a nick translation polymerase Phi29.

In some embodiments, the first single-stranded nick and the second single-stranded nick are on opposite strands of the target DNA sequence, thereby generating a first double-stranded DNA break end.

In some embodiments, the first region of the target nucleic acid and the second region of the target nucleic acid are on the same strand of the target nucleic acid; the first Cas protein is a first Cas9 protein with one inactivated nuclease domain having a first mutation in the domain that cleaves a target nucleic acid strand that is complementary to the first crRNA, and the second Cas protein is a second Cas9 protein with one inactivated nuclease domain having a second mutation in the domain that cleaves a target nucleic acid strand that is non-complementary to the second crRNA. In some embodiments, the first mutation is D10A, and the second mutation is H840A.

In some embodiments, the first region of the target nucleic acid and the second region of the target nucleic acid are on opposite strands of the target nucleic acid; first Cas protein is a first Cas9 protein containing one inactivated nuclease domain having a first mutation in the domain that cleaves a target nucleic acid strand that is complementary to the first crRNA, and the second Cas protein is a second Cas9 protein containing one inactivated nuclease domain containing a second mutation in the domain that cleaves a target nucleic acid strand that is complementary to the second crRNA. In some embodiments, both the first mutation and the second mutation are D10A.

In some embodiments, the first region of the target nucleic acid and the second region of the target nucleic acid are on opposite strands of the target nucleic acid; the first Cas protein is a first Cas9 protein containing one inactivated nuclease domain having a first mutation in the domain that cleaves a target nucleic acid strand that is non-complementary to the first crRNA, and the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, nicks are made at relatively close nucleic acid positions, and a blunt ended break can be produced. In some embodiments, nicks are made at relatively far away from each other, and a sticky ended break with 5' or 3' overhangs can be produced. In some embodiments, the method of the present disclosure further includes ligating an adaptor to the double-stranded nucleic acid break end. In some embodiments, the adaptor of the present disclosure is biotinylated. In some embodiments, the method of the present disclosure includes adding magnetic streptavidin beads to enrich the target nucleic acid.

In some embodiments, the method provided herein further includes providing a third nuclease system having a third crRNA or a derivative thereof, and a third Cas protein or a variant thereof, wherein the third crRNA or the derivative thereof contains a third target-specific nucleotide region substantially complementary to a third region of the target nucleic acid, and wherein the third Cas protein contains one inactivated nuclease domain; providing a fourth nuclease system having a fourth crRNA or a derivative thereof, and a fourth Cas protein or a variant thereof, wherein the fourth crRNA or the derivative thereof contains a fourth target-specific nucleotide region substantially complementary to a fourth region of the target nucleic acid, and wherein the fourth Cas protein contains one inactivated nuclease domain; and contacting the double-stranded nucleic acid containing the target nucleic acid with the third and fourth nuclease systems to generate a third single-stranded nick at the third region of the target nucleic acid and a fourth single-stranded nick at the fourth region of the target nucleic acid, wherein in the third single-stranded nick and the fourth single-stranded nick are on opposite strands of the target nucleic acid, thereby generating a second double-stranded nucleic acid break end, the second double-stranded nucleic acid break end being different from the first double-stranded nucleic acid break end.

In other embodiments, the method provided herein further includes providing a third nuclease system having: a third 5' phosphorylated single-stranded nucleic acid or a derivative thereof, and a third Argonaute protein or a variant thereof, wherein the third 5' phosphorylated single-stranded nucleic acid or the derivative thereof contains a third target-specific nucleotide region substantially complementary to a third region of the target nucleic acid, and wherein the third Argonaute protein is capable of generating a single-stranded nick; providing a fourth nuclease system having: a fourth 5' phosphorylated single-stranded nucleic acid or a derivative thereof, and a fourth Argonaute protein or a variant thereof, wherein the fourth 5' phosphorylated single-stranded nucleic acid or the derivative thereof contains a fourth target-specific nucleotide region substantially complementary to a fourth region of the target nucleic acid, and wherein the fourth Argonaute protein is capable of generating a single-stranded nick; and contacting the double-stranded nucleic acid containing the target nucleic acid with the third and fourth nuclease systems to generate a third single-stranded nick at the third region of the target nucleic acid and a fourth single-stranded nick at the fourth region of the target nucleic acid, wherein in the third single-stranded nick and the fourth single-stranded nick are on opposite strands of the target nucleic acid, thereby generating a second double-stranded nucleic acid break end, the second double-stranded nucleic acid break end being different from the first double-stranded nucleic acid break end.

In some embodiments, the nucleic acid fragment between the first and second double-stranded nucleic acid break ends can contain from 10 to multiple thousands of nucleotides. In some embodiments, capture probes, such as single-stranded oligos, DNA dumbbells, and double-stranded DNA adapters can be added to label the nucleic acid fragment. In some embodiments, the method provided herein further includes ligating an adapter to the second double-stranded nucleic acid break end.

For example, two pairs of CRISPR-Cas systems or Argonaute systems are provided. Each pair of enzymes contains two nickases, e.g., Cas9 nickases or Argonaute nickases, and the two nickases can generate single-stranded DNA nicks on opposite strands of DNA. As such, each pair of enzymes generates a double-stranded DNA break end, and two double-stranded DNA break ends are generated surrounding or at the two ends of the target DNA sequence. In one embodiment, the DNA fragment between the two double-stranded DNA break ends is about 10 kb. In some embodiments, the DNA fragment between the two double-stranded DNA break ends is about 1 kb, 2 kb, 3 kb, 4 kb, 5 kb, 6 kb, 7 kb, 8 kb, or 9 kb. The DNA fragment can be further ligated to target-specific biotinylated PCR adapters through which the target DNA can be enriched.

The enriched double-stranded nucleic acid can be further subject to sequencing. In one embodiment, the enriched DNA is tagmented to smaller fragments and introduced to sequencing adapters. In some embodiments, the method provided herein further includes dilution prior to tagmentation. In one embodiment, the enriched DNA is diluted to haploid content prior to PCR and/or tagmentation.

In some embodiments, Nextera library preparation (available from Illumina, Inc, San Diego, Calif.) is performed to fragment input DNA and introduce sequencing primers, and then the fragmented DNA is contacted with the CRISPR-Cas or Argonaute system provided herein to form a complex. The complex is pulled down and the target DNA can be released from the complex, e.g., using EDTA, heat, SDS, and RNase. The sequencing can then be performed.

In another aspect, the present disclosure provides a method of enriching double-stranded DNA using multiple CRISPR-Cas or Argonaute systems which retain full endonuclease activity (i.e., being capable of generating double-stranded breaks), e.g., multiple CRISPR-Cas systems each of which having wild-type Cas9 containing two nuclease domains.

In some embodiments, provided herein is a method for enriching a target nucleic acid including: providing a population of Cas9 proteins programmed with a set of crRNAs, wherein the set of crRNAs contains crRNAs complementary to a series of different regions of the target nucleic acid; contacting the target nucleic acid with the population of Cas9 proteins programmed with the set of crRNAs to generate a series of nucleic acid fragments, and ligating adaptors to at least one of nucleic acid fragments, wherein the Cas9 protein retains two nuclease domains.

In other embodiments, provided herein is a method for enriching a target nucleic acid including: providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions of the target nucleic acid; contacting the target nucleic acid with the population of Argonaute proteins programmed with the set of 5' phosphorylated single-stranded nucleic acids to generate a series of nucleic acid fragments, and ligating adaptors to at least one of nucleic acid fragments, wherein the Argonaute proteins are capable of generating double-stranded DNA breaks.

In some embodiments, the set of crRNAs contains crRNAs complementary to two different regions of the target nucleic acid. In some embodiments, the set of 5' phosphorylated single-stranded nucleic acids contains 5' phosphorylated single-stranded nucleic acids complementary to two different regions of the target nucleic acid.

The method provided herein can be useful for enriching a long DNA fragment. In some embodiments, the space between the two different region is longer than 10 kb.

In some embodiments, the target nucleic acid is a double-stranded DNA. In some embodiments, the target nucleic acid is a genomic DNA, a chromosomal DNA, a genome, or a partial genome.

In another aspect, the present disclosure provides a method of Cas9 or Argonaute mediated nucleic acid fragmentation and targeted sequencing. The present disclosure provides a method for fragmenting DNA in a sequence specific manner in user defined regions, and generating nucleic acid fragments for subsequent sequencing, e.g., DNA fragments amendable for incorporation into Illumina's sequencing libraries.

In some embodiments, the method for sequencing a target nucleic acid provided herein includes providing a population of Cas9 proteins programmed with a set of crRNAs, wherein the set of crRNAs contains crRNAs complementary to a series of different regions across the target nucleic acid; contacting the target nucleic acid with the population of Cas9 proteins programmed with the set of crRNAs to generate a series of nucleic acid fragments, and sequencing the series of nucleic acid fragments.

In other embodiments, the method for sequencing a target nucleic acid provided herein includes providing a population of Argonaute proteins programmed with a set of 5' phosphorylated single-stranded nucleic acids, wherein the set of 5' phosphorylated single-stranded nucleic acids contains 5' phosphorylated single-stranded nucleic acids complementary to a series of different regions across the target nucleic acid; contacting the target nucleic acid with the population of Argonaute proteins programmed with the set of 5' phosphorylated single-stranded nucleic acids to generate a series of nucleic acid fragments, and sequencing the series of nucleic acid fragments.

In some embodiments, targeted fragmentation of nucleic acid can be achieved by preparing a population of Cas9 or Argonaute proteins that are programmed with guide nucleic acids targeting regions tiled across the target nucleic acid. In some embodiments, the Cas9 or Argonaute proteins provided herein can generate double-stranded nucleic acid breaks and thus a series of nucleic acid fragments. These nucleic acid fragments can be further subjected to nucleic acid sequencing workflows.

The same nucleic acid sample can be treated separately with multiple populations of Cas9 or Argonaute proteins programmed with different sets of guide nucleic acid targeting regions tiled across the target nucleic acid. The nucleic acid fragments generated by each population overlap with nucleic acid fragments generated by another population. More reliable and comprehensive sequencing data can be achieved by sequencing nucleic acid fragments with overlapping sequences.

In some embodiments, the method for sequencing a target nucleic acid provided herein includes providing a plurality of populations of Cas9 proteins, each population of Cas9 proteins being programmed with a different set of crRNAs, wherein each set of crRNAs contains crRNAs complementary to a different series of regions across the target nucleic acid; contacting the target nucleic acid with each of the plurality of populations of Cas9 proteins in a separate reaction to generate a different series of nucleic acid fragments, and sequencing the nucleic acid fragments.

In other embodiments, the method for sequencing a target nucleic acid provided herein includes providing a plurality of populations of Argonaute proteins, each population of Argonaute proteins being programmed with a different set of 5' phosphorylated single-stranded nucleic acids, wherein each set of 5' phosphorylated single-stranded nucleic acids contains 5' phosphorylated single-stranded nucleic acids complementary to a different series of regions across the target nucleic acid, contacting the target nucleic acid with each of the plurality of populations of Argonaute proteins in a separate reaction to generate a different series of nucleic acid fragments, and sequencing the nucleic acid fragments.

In some embodiments, the plurality of populations of Cas9 or Argonaute proteins includes three populations of Cas9 or Argonaute proteins, and wherein the nucleic acid fragments generated by each of the three populations of Cas9 or Argonaute proteins contain overlapping sequences with the nucleic acid fragments generated by at least another of the three populations of Cas9 proteins. For example, a 10 kb target DNA can be treated with the Cas9 proteins programmed with three sets of crRNAs targeting regions with about 500 bp intervals across the target DNA sequence. Each set of crRNAs contains about 57 crRNAs. Cas9 proteins remain non-covalently associated with the ends of cleaved DNAs, cleaved target DNA can be released by treatment of the sample with protease or detergent. Cleavage products are then pooled and converted to sequencing libraries, e.g., using Illumina's TruSeq Nano workflow. The cleavage can be carried out using a different set of crRNAs in a separate reaction. For instance, cleavage can be carried out in 3 tubes (Pot 1, Pot 2, and Pot 3) with three libraries of Cas9 complexes reconstituted with cRNAs that generate overlapping fragments about 500 bp in size. Such overlapping fragments can improve the sequencing accuracy.

In some embodiments, the present disclosure provides a method for targeted haplotype sequencing (phased sequencing). In some embodiments, the method provided herein further includes diluting a DNA sample containing the target DNA to haploid content. Phase or haplotype information, which refers to the unique content of the two homologous chromosomes in diploid organisms, provides a useful tool to better understand relationships between human DNA sequence and phenotype, including diseases. The present disclosure provides a method for haplotype sequencing using CRISPR-Cas or Argonaute systems. A haplotype sequencing workflow can take advantage of the ability of Cas9 or Argonaute proteins to hold onto ends of cleaved DNA. Since Cas9 or Argonaute proteins remain association with the ends of cleaved DNAs, this creates a haplotype block of DNA proportional in size to the number and distance between Cas9 or Argonaute target regions in a target sequence. In some embodiments, following cleave, reactions can be diluted in microtiter wells to subhaplotype levels, and then can be treated with protease to release joined fragments anc converted into a sequencing library, e.g., using TruSeq Nano library preparation method available from Illumina, Inc. (San Diego, Calif.).

In some embodiments, the target nucleic acid provided herein is a double-stranded DNA. In some embodiments, the target nucleic acid provided herein is a genomic DNA, a chromosomal DNA, a genome, or a partial genome.

In some embodiments, the nucleic acid fragments can be amplified, e.g., using limited-cycle polymerase chain reaction (PCR), to introduce other end sequences or adaptors, e.g., index, universal primers and other sequences required for cluster formation and sequencing.

In some embodiments, the sequencing the nucleic acid fragments includes use of one or more of sequencing by synthesis, bridge PCR, chain termination sequencing, sequencing by hybridization, nanopore sequencing, and sequencing by ligation.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

Additional Embodiments

Embodiment 1. A method for amplifying a target double-stranded nucleic acid comprising:
(a) providing a system having:
a clustered regularly interspaced short palindromic repeats (CRISPR) RNA (crRNA) or a derivative thereof, and
a CRISPR-associated (Cas) protein or a variant thereof, wherein the crRNA or the derivative thereof contains a target-specific nucleotide region complementary to a region of a first strand of the target double-stranded nucleic acid;
(b) contacting the target double-stranded nucleic acid with the system to form a complex;
(c) hybridizing a primer to a second strand of the target double-stranded nucleic acid, the primer containing a sequence complementary to a region of the second strand of the target double-stranded nucleic acid, and
(d) extending a nucleic acid complementary to the second strand of the target double-stranded nucleic acid from the primer using a polymerase.

Embodiment 2. The method of Embodiment 1, further comprising repeating step (a) to step (d) for one or more times.

Embodiment 3. The method of Embodiment 1, wherein the target double-stranded nucleic acid is linearly amplified.

Embodiment 4. The method of Embodiment 1, wherein the target double-stranded nucleic acid is exponentially amplified.

Embodiment 5. The method of Embodiment 1, wherein the target nucleic acid is a double-stranded DNA (dsDNA).

Embodiment 6. The method of Embodiment 1, wherein the target nucleic acid is a double-stranded RNA (dsRNA).

Embodiment 7. The method of Embodiment 1, wherein the system is a Type I CRISPR-Cas system or a derivative thereof.

Embodiment 8. The method of Embodiment 1, wherein the system is a Type II CRISPR-Cas system or a derivative thereof.

Embodiment 9. The method of Embodiment 1, wherein the system is a Type III CRISPR-Cas system or a derivative thereof.

Embodiment 10. The method of Embodiment 1, wherein the system further comprises a trans-activating crRNA (tracrRNA) or a derivative thereof.

Embodiment 11. The method of Embodiment 1, wherein the crRNA or the derivative thereof is a polynucleotide comprising a crRNA polynucleotide fused to a tracrRNA polynucleotide.

Embodiment 12. The method of Embodiment 1, wherein the first strand of the target double-stranded nucleic acid contains a sequence complementary to a 5'-NGG protospacer-adjacent motif (PAM).

Embodiment 13. The method of Embodiment 1, wherein the first strand of the target double-stranded nucleic acid contains a universal sequence, and wherein the crRNA or the derivative thereof contains a sequence complementary to a region of the universal sequence.

Embodiment 14. The method of Embodiment 13, wherein the primer contains a sequence of a region of the universal sequence.

Embodiment 15. The method of Embodiment 13, wherein the universal sequence has a sequence of SEQ ID No. 3.

Embodiment 16. The method of Embodiment 15, wherein the crRNA contains a sequence of SEQ ID No. 7.

Embodiment 17. The method of Embodiment 16, wherein the primer contains a sequence of SEQ ID No. 5.

Embodiment 18. The method of Embodiment 13, wherein the universal sequence has a sequence of SEQ ID No. 4.

Embodiment 19. The method of Embodiment 18, wherein the crRNA contains a sequence of SEQ ID No. 8.

Embodiment 20. The method of Embodiment 19, wherein the primer contains a sequence of SEQ ID No. 6.

Embodiment 21. The method of Embodiment 1, wherein the Cas protein or the variant thereof is a Cas9 protein or a variant thereof.

Embodiment 22. The method of Embodiment 21, wherein the Cas9 protein contains two inactivated nuclease domains.

Embodiment 23. The method of Embodiment 22, wherein the two inactivated nuclease domains comprise a first mutation in the domain that cleaves the strand complementary to the crRNA and a second mutation in the domain that cleaves the strand non-complementary to the crRNA.

Embodiment 24. The method of Embodiment 23, wherein the first mutation is D10A and the second mutation is H840A.

Embodiment 25. The method of Embodiment 1, wherein the Cas protein or the variant thereof is a Cascade protein or a variant thereof.

Embodiment 26. The method of Embodiment 1, wherein the Cas protein or the variant thereof is a Cas3 protein or a variant thereof.

Embodiment 27. The method of Embodiment 1, wherein the polymerase is a strand-displacing polymerase.

Embodiment 28. The method of Embodiment 27, wherein the polymerase is selected from a group consisting of Bst, Bsu, and Phi29.

Embodiment 29. The method of Embodiment 1, further comprising:
applying at least one transposase and at least one transposon end composition containing a transferred strand to a sample containing a target nucleic acid under conditions where the target nucleic acid and the transposon end composition undergo a transposition reaction to generate a mixture, wherein the target nucleic acid is fragmented to generate a plurality of target nucleic acid fragments, and
incorporating a universal primer sequence into each of the plurality of target nucleic acid fragments,
wherein the crRNA or the derivative thereof contains a target-specific nucleotide region complementary to a region of the universal primer.

Embodiment 30. The method of Embodiment 29, wherein the universal primer is incorporated into the plurality of target nucleic acid fragments by a PCR reaction.

Embodiment 31. The method of Embodiment 30, wherein the universal primer has sequence complementary to a 5'-NGG protospacer-adjacent motif (PAM).

Embodiment 32. The method of Embodiment 30, wherein the universal sequence has a sequence of SEQ ID No. 3.

Embodiment 33. The method of Embodiment 32, wherein the crRNA contains a sequence of SEQ ID No. 7.

Embodiment 34. The method of Embodiment 33, wherein the primer contains a sequence of SEQ ID No. 5.

Embodiment 35. The method of Embodiment 30, wherein the universal primer has a sequence of SEQ ID No. 4.

Embodiment 36. The method of Embodiment 35, wherein the crRNA contains a sequence of SEQ ID No. 8.

Embodiment 37. The method of Embodiment 36, wherein the primer contains a sequence of SEQ ID No. 6.

Embodiment 38. The method of Embodiment 29, wherein two universal primers are incorporated into two ends of each of the plurality of target nucleic acid fragments.

Embodiment 39. The method of Embodiment 38, wherein the two universal primers have sequences of SEQ ID No. 3 and SEQ ID No. 4.

Embodiment 40. A method for amplifying a target double-stranded nucleic acid comprising:
(a) providing a first system having:
a first clustered regularly interspaced short palindromic repeats (CRISPR) RNA (crRNA) or a derivative thereof, and
a first CRISPR-associated (Cas) protein or a variant thereof,
wherein the first crRNA or the derivative thereof contains a target-specific nucleotide region complementary to a region of a first strand of the target double-stranded nucleic acid;
(b) providing second system having:
a second clustered regularly interspaced short palindromic repeats (CRISPR) RNA (crRNA) or a derivative thereof, and
a second CRISPR-associated (Cas) protein or a variant thereof,
wherein the second crRNA or the derivative thereof contains a target-specific nucleotide region complementary to a region of a second strand of the target double-stranded nucleic acid;

(c) contacting the target double-stranded nucleic acid with the first system and the second system;

(d) hybridizing a first primer to a second strand of the target double-stranded nucleic acid, the first primer containing a sequence complementary to a region of the second strand of the target double-stranded nucleic acid, and hybridizing a second primer to a first strand of the target double-stranded nucleic acid, the second primer containing a sequence complementary to a region of the first strand of the target double-stranded nucleic acid, and (e) extending the 3' end of the first primer and the second primer with one or more polymerases to generate a first and a second double stranded target nucleic acid.

Embodiment 41. The method of Embodiment 40, further comprising repeating step (a) to step (e) for one or more times.

Embodiment 42. The method of Embodiment 40, wherein the target nucleic acid is a double-stranded DNA (dsDNA).

Embodiment 43. The method of Embodiment 40, wherein the target nucleic acid is a double-stranded RNA (dsRNA).

Embodiment 44. The method of Embodiment 40, wherein the first system or the second system is a Type I CRISPR-Cas system or a derivative thereof.

Embodiment 45. The method of Embodiment 40, wherein the first system or the second system is a Type II CRISPR-Cas system or a derivative thereof.

Embodiment 46. The method of Embodiment 40, wherein the first system or a second system is a Type III CRISPR-Cas system or a derivative thereof.

Embodiment 47. The method of Embodiment 40, wherein the first system or the second system further comprises a trans-activating crRNA (tracrRNA) or a derivative thereof.

Embodiment 48. The method of Embodiment 40, wherein the crRNA or the derivative thereof of the first system or the second system is a polynucleotide comprising a crRNA polynucleotide fused to a tracrRNA polynucleotide.

Embodiment 49. The method of Embodiment 40, wherein the first strand and the second strand of the target double-stranded nucleic acid contain a sequence complementary to a 5'-NGG protospacer-adjacent motif (PAM).

Embodiment 50. The method of Embodiment 40, wherein:
the first strand of the target double-stranded nucleic acid contains a first universal sequence, and wherein the crRNA or the derivative thereof of the first system contains a sequence complementary to a region of the first universal sequence, and the second strand of the target double-stranded nucleic acid contains a second universal sequence, and wherein the crRNA or the derivative thereof of the second system contains a sequence complementary to a region of the second universal sequence.

Embodiment 51. The method of Embodiment 50, wherein the first primer contains a sequence of a region of the first universal sequence, and the second primer contains a sequence of a region of the second universal sequence.

Embodiment 52. The method of Embodiment 51, wherein:
the first universal sequence has a sequence of SEQ ID No. 3, the crRNA or the derivative thereof of the first system contains a sequence of SEQ ID No. 7, and the first primer contains a sequence of SEQ ID No. 5, and the second universal sequence has a sequence of SEQ ID No. 4, the crRNA or derivative thereof of the second system contains a sequence of SEQ ID No. 8, and the second primer contains a sequence of SEQ ID No. 6.

Embodiment 53. The method of Embodiment 40, wherein the Cas protein or the variant thereof of the first system or the second system is a Cas9 protein or a variant thereof.

Embodiment 54. The method of Embodiment 53, wherein the Cas9 protein contains two inactivated nuclease domains.

Embodiment 55. The method of Embodiment 54, wherein the two inactivated nuclease domains comprise a first mutation in the domain that cleaves the strand complementary to the crRNA and a second mutation in the domain that cleaves the strand non-complementary to the crRNA.

Embodiment 56. The method of Embodiment 55, wherein the first mutation is D10A and the second mutation is H840A.

Embodiment 57. The method of Embodiment 40, wherein the Cas protein or the variant thereof of the first system or the second system is a Cascade protein or a variant thereof.

Embodiment 58. The method of Embodiment 40, wherein the Cas protein or the variant thereof of the first system or the second system is a Cas3 protein or a variant thereof.

Embodiment 59. The method of Embodiment 40, wherein the polymerase is a strand-displacing polymerase.

Embodiment 60. The method of Embodiment 59, wherein the polymerase is selected from a group consisting of Bst, Bsu, and Phi29.

Embodiment 61. The method of any one of Embodiments 1-60, wherein the target nucleic acid is genomic DNA.

Embodiment 62. The method of any one of Embodiments 1-60, wherein the target nucleic acid contains chromosomal DNA or a fragment thereof.

Embodiment 63. The method of any one of Embodiments 1-60, wherein the target nucleic acid comprises a genome or a partial genome.

Embodiment 64. The method of any one of Embodiments 1-63, further comprising sequencing the target nucleic acid or target nucleic acid fragments.

Embodiment 65. The method of Embodiment 64, wherein the sequencing comprises use of one or more of sequencing by synthesis, bridge PCR, chain termination sequencing, sequencing by hybridization, nanopore sequencing, and sequencing by ligation.

Embodiment 96. The method of any one of Embodiments 1-65, further comprising sequencing the target nucleic acid or target nucleic acid fragments.

Embodiment 97. The method of Embodiment 96, wherein the sequencing comprises use of one or more of sequencing by synthesis, bridge PCR, chain termination sequencing, sequencing by hybridization, nanopore sequencing, and sequencing by ligation.

What is claimed:

1. A method for amplifying a target double-stranded nucleic acid comprising:
    (a) applying at least one transposase and at least one transposon end composition containing a transferred strand to a sample containing a target polynucleotide under conditions where the target polynucleotide and the transposon end composition undergo a transposition reaction to generate a mixture, wherein the target polynucleotide is fragmented to generate a plurality of target double-stranded nucleic acids, and incorporating a universal primer sequence into each of the plurality of target double-stranded nucleic acids;
    (b) providing a system having:
        a guide nucleic acid, wherein the guide nucleic acid is a 5' phosphorylated single-stranded nucleic acid or a derivative thereof, and
        an Argonaute protein or a variant thereof,
        wherein the guide nucleic acid contains a target-specific nucleotide region complementary to a universal primer sequence in a first strand of a target double-stranded nucleic acid of the plurality of target double-stranded nucleic acids;
    (c) contacting the target double-stranded nucleic acid with the system to form a loop comprising the first region hybridized to the guide nucleic acid and a second region of a second strand of the target double-stranded nucleic acid, wherein the second region is displaced from the first region;
    (d) hybridizing a primer to the second region, wherein the primer comprises a sequence complementary to the second region, and
    (e) extending the hybridized primer with a polymerase to obtain a nucleic acid complementary to the second strand of the target double-stranded nucleic acid.

2. The method of claim 1, further comprising repeating step (b) to step (e) for one or more times.

3. The method of claim 1, wherein the target double-stranded nucleic acid is linearly amplified.

4. The method of claim 1, wherein the target double-stranded nucleic acid is exponentially amplified.

5. The method of claim 1, wherein the target nucleic acid is a double-stranded DNA (dsDNA).

6. The method of claim 1, wherein the target nucleic acid is a double-stranded RNA (dsRNA).

7. The method of claim 1, wherein the Argonaute protein is Natronobacterium gregoryi Argonaute (Ng Argonaute).

8. The method of claim 1, wherein the guide nucleic acid is a single-stranded DNA of less than 25 nucleotides.

9. The method of claim 1, wherein the polymerase is a strand-displacing polymerase.

10. A method for amplifying a target double-stranded nucleic acid comprising:
   (a) providing a first system having:
      a first 5' phosphorylated single-stranded nucleic acid or a derivative thereof, and
      a first Argonaute protein or a variant thereof,
      wherein the first 5' phosphorylated single-stranded nucleic acid or the derivative thereof contains a target-specific nucleotide region complementary to a region of a first strand of the target double-stranded nucleic acid;
   (b) providing second system having:
      a second 5' phosphorylated single-stranded nucleic acid or a derivative thereof, and
      a second Argonaute protein or a variant thereof,
      wherein the second 5' phosphorylated single-stranded nucleic acid or the derivative thereof contains a target-specific nucleotide region complementary to a region of a second strand of the target double-stranded nucleic acid;
   (c) contacting the target double-stranded nucleic acid with the first system to form a first complex comprising a first displaced region of the second strand of the target double-stranded nucleic acid, and with the second system to form a second complex comprising a second displaced region of the first strand of the target double-stranded nucleic acid;
   (d) hybridizing a first primer to the first displaced region, wherein the first primer comprises a sequence complementary to the first displaced region, and hybridizing a second primer to the second displaced region, wherein the second primer comprises a sequence complementary to the second displaced region; and
   (e) extending the 3' end of the first primer and the second primer with a polymerase to generate a first and a second double stranded target nucleic acid.

11. The method of claim 10, further comprising repeating step (a) to step (e) for one or more times.

12. The method of claim 10, wherein the target nucleic acid is a double-stranded DNA (dsDNA).

13. The method of claim 10, wherein the target nucleic acid is a double-stranded RNA (dsRNA).

14. The method of claim 10, wherein the first and the second Argonaute proteins are Natronobacterium gregoryi Argonaute (Ng Argonautes).

15. The method of claim 10, wherein the first and the second 5' phosphorylated single-stranded nucleic acids are single-stranded DNAs of less than 25 nucleotides.

16. The method of claim 10, wherein:
   the first strand of the target double-stranded nucleic acid contains a first universal sequence, and wherein the first 5' phosphorylated single-stranded nucleic acid or the derivative thereof of the first system contains a sequence complementary to a region of the first universal sequence, and
   the second strand of the target double-stranded nucleic acid contains a second universal sequence, and wherein the second 5' phosphorylated single-stranded nucleic acid or the derivative thereof of the second system contains a sequence complementary to a region of the second universal sequence.

17. The method of claim 10, wherein the first primer contains a sequence of a region of a first universal sequence, and the second primer contains a sequence of a region of a second universal sequence.

18. The method of claim 10, wherein the polymerase is a strand-displacing polymerase.

19. The method of claim 1, wherein step ((d)) is performed in the presence of the Argonaute protein or a variant thereof.

20. The method of claim 1, wherein steps ((d)) and ((e)) are performed in the presence of the Argonaute protein or a variant thereof.

* * * * *

SEQUENCE LISTING

<160> NUMBER OF SEQ ID NOS: 15

<210> SEQ ID NO 1

-continued

```
<211> LENGTH: 29
<212> TYPE: DNA
<213> ORGANISM: Artificial Sequence
<220> FEATURE:
<223> OTHER INFORMATION: Standard P5 sequence

<400> SEQUENCE: 1
aatgatacgg cgaccaccga gatctacac                                      29

<210> SEQ ID NO 2
<211> LENGTH: 24
<212> TYPE: DNA
<213> ORGANISM: Artificial Sequence
<220> FEATURE:
<223> OTHER INFORMATION: Standard P7 sequence

<400> SEQUENCE: 2
caagcagaag acggcatacg agat                                           24

<210> SEQ ID NO 3
<211> LENGTH: 32
<212> TYPE: DNA
<213> ORGANISM: Artificial Sequence
<220> FEATURE:
<223> OTHER INFORMATION: PAM-Modified P5 sequence
<220> FEATURE:
<221> NAME/KEY: misc_feature
<222> LOCATION: 3
<223> OTHER INFORMATION: n = A,T,C or G

<400> SEQUENCE: 3
ccnaatgata cggcgaccac cgagatctac ac                                  32

<210> SEQ ID NO 4
<211> LENGTH: 27
<212> TYPE: DNA
<213> ORGANISM: Artificial Sequence
<220> FEATURE:
<223> OTHER INFORMATION: PAM-Modified P7 sequence
<220> FEATURE:
<221> NAME/KEY: misc_feature
<222> LOCATION: 3
<223> OTHER INFORMATION: n = A,T,C or G

<400> SEQUENCE: 4
ccncaagcag aagacggcat acgagat                                        27

<210> SEQ ID NO 5
<211> LENGTH: 21
<212> TYPE: DNA
<213> ORGANISM: Artificial Sequence
<220> FEATURE:
<223> OTHER INFORMATION: Truncated PAM-Modified P5 sequence
<220> FEATURE:
<221> NAME/KEY: misc_feature
<222> LOCATION: 3
<223> OTHER INFORMATION: n = A,T,C or G

<400> SEQUENCE: 5
ccnaatgata cggcgaccac c                                              21

<210> SEQ ID NO 6
<211> LENGTH: 21
<212> TYPE: DNA
<213> ORGANISM: Artificial Sequence
<220> FEATURE:
<223> OTHER INFORMATION: Truncated PAM-Modified P7 sequence
<220> FEATURE:
<221> NAME/KEY: misc_feature
```

```
<222> LOCATION: 3
<223> OTHER INFORMATION: n = A,T,C or G

<400> SEQUENCE: 6
ccncaagcag aagacggcat a                                             21

<210> SEQ ID NO 7
<211> LENGTH: 20
<212> TYPE: RNA
<213> ORGANISM: Artificial Sequence
<220> FEATURE:
<223> OTHER INFORMATION: Guide RNA P5 targeting

<400> SEQUENCE: 7
ucgguggucg ccguaucauu                                               20

<210> SEQ ID NO 8
<211> LENGTH: 20
<212> TYPE: RNA
<213> ORGANISM: Artificial Sequence
<220> FEATURE:
<223> OTHER INFORMATION: Guide RNA P7 targeting

<400> SEQUENCE: 8
cguaugccgu cuucugcuug                                               20

<210> SEQ ID NO 9
<211> LENGTH: 32
<212> TYPE: DNA
<213> ORGANISM: Artificial Sequence
<220> FEATURE:
<223> OTHER INFORMATION: DNA to be amplified which possesses primer
      sequence P5

<400> SEQUENCE: 9
cctaatgata cggcgaccac cgagatctac ac                                 32

<210> SEQ ID NO 10
<211> LENGTH: 27
<212> TYPE: DNA
<213> ORGANISM: Artificial Sequence
<220> FEATURE:
<223> OTHER INFORMATION: DNA to be amplified which possesses primer
      sequence P7

<400> SEQUENCE: 10
atctcgtatg ccgtcttctg cttgagg                                       27

<210> SEQ ID NO 11
<211> LENGTH: 19
<212> TYPE: RNA
<213> ORGANISM: Artificial Sequence
<220> FEATURE:
<223> OTHER INFORMATION: guide RNA targeting P5

<400> SEQUENCE: 11
uuacuaugcc gugguggcu                                                19

<210> SEQ ID NO 12
<211> LENGTH: 26
<212> TYPE: DNA
<213> ORGANISM: Artificial Sequence
<220> FEATURE:
<223> OTHER INFORMATION: includes immobilized P5 primer
<220> FEATURE:
<221> NAME/KEY: misc_feature
<222> LOCATION: 1, 2, 3, 4, 5
```

```
<223> OTHER INFORMATION: n = A,T,C or G

<400> SEQUENCE: 12
nnnnncctaa tgatacggcg accacc                                              26

<210> SEQ ID NO 13
<211> LENGTH: 37
<212> TYPE: DNA
<213> ORGANISM: Artificial Sequence
<220> FEATURE:
<223> OTHER INFORMATION: extended primer P5
<220> FEATURE:
<221> NAME/KEY: misc_feature
<222> LOCATION: 1, 2, 3, 4, 5
<223> OTHER INFORMATION: n = A,T,C or G

<400> SEQUENCE: 13
nnnnncctaa tgatacggcg accaccgaga tctacac                                  37

<210> SEQ ID NO 14
<211> LENGTH: 26
<212> TYPE: DNA
<213> ORGANISM: Artificial Sequence
<220> FEATURE:
<223> OTHER INFORMATION: includes immobilized P7 primer
<220> FEATURE:
<221> NAME/KEY: misc_feature
<222> LOCATION: 1, 2, 3, 4, 5
<223> OTHER INFORMATION: n = A,T,C or G

<400> SEQUENCE: 14
nnnnntccca agcagaagac ggcata                                              26

<210> SEQ ID NO 15
<211> LENGTH: 32
<212> TYPE: DNA
<213> ORGANISM: Artificial Sequence
<220> FEATURE:
<223> OTHER INFORMATION: Includes extended primer P7
<220> FEATURE:
<221> NAME/KEY: misc_feature
<222> LOCATION: 1, 2, 3, 4, 5
<223> OTHER INFORMATION: n = A,T,C or G

<400> SEQUENCE: 15
nnnnntccca agcagaagac ggcatacgag at                                       32
```